(12) United States Patent
Wen et al.

(10) Patent No.: US 12,054,794 B2
(45) Date of Patent: Aug. 6, 2024

(54) TRANSCRIPTION MEDIATED AMPLIFICATION METHODS FOR RNA DETECTION

(71) Applicants: Fushi Wen, Tucson, AZ (US); Frederick H. Eggers, Sahuarita, AZ (US); Michael E. Hogan, Stony Brook, NY (US)

(72) Inventors: Fushi Wen, Tucson, AZ (US); Frederick H. Eggers, Sahuarita, AZ (US); Michael E. Hogan, Stony Brook, NY (US)

(*) Notice: Subject to any disclaimer, the term of this patent is extended or adjusted under 35 U.S.C. 154(b) by 0 days.

(21) Appl. No.: 17/840,835

(22) Filed: Jun. 15, 2022

(65) Prior Publication Data

US 2022/0403476 A1 Dec. 22, 2022

Related U.S. Application Data

(60) Provisional application No. 63/210,934, filed on Jun. 15, 2021.

(51) Int. Cl.

| | |
|---|---|
| *C12Q 1/70* | (2006.01) |
| *C12Q 1/6818* | (2018.01) |
| *C12Q 1/6837* | (2018.01) |
| *C12Q 1/6853* | (2018.01) |
| *C12Q 1/689* | (2018.01) |

(52) U.S. Cl.
CPC ........... *C12Q 1/701* (2013.01); *C12Q 1/6837* (2013.01); *C12Q 1/6818* (2013.01); *C12Q 1/6853* (2013.01); *C12Q 1/689* (2013.01); *C12Q 2600/16* (2013.01)

(58) Field of Classification Search
CPC .... C12Q 1/701; C12Q 1/6837; C12Q 1/6818; C12Q 2600/16; C12Q 2531/143
See application file for complete search history.

(56) References Cited

U.S. PATENT DOCUMENTS

2018/0251758 A1* 9/2018 Hogan ................ C12Q 1/6837

OTHER PUBLICATIONS

Xing (Engineering 6, 2020, pp. 1130-1140).*
Wu (Sci Adv, 2021, vol. 7, p. 1-13).*
Yoo (Int. J. Mol. Sci, 2021, 22, p. 6150, pp. 1-25).*

* cited by examiner

*Primary Examiner* — Sarae L Bausch
(74) *Attorney, Agent, or Firm* — Benjamin Aaron Adler

(57) ABSTRACT

Provided herein is a method for detecting the presence of a COVID-19 virus RNA or other pathogenic respiratory viruses, such as an influenza virus, or other RNA of interest in a sample. Nucleic acids are obtained from the sample and are used as a template in a combined isothermal reverse transcription, RNAse H and isothermal amplification reaction to generate single stranded RNA amplicons containing sequences complementary to fluorescent labeled detector probes. The single-stranded RNA amplicons hybridize to the detector probe and to hybridization probes with sequences complementary to a sequence determinant in the COVID-19 or other virus RNAs. The microarray is imaged to detect fluorescent signals thereby identifying the virus.

25 Claims, 15 Drawing Sheets

Specification includes a Sequence Listing.

● Cv Ct for correct Variant ID   ● Cv Ct

Bar keys
- Universal probe
- Wild type probe
- Mutant probe

SEQUENCE LISTING

<160> NUMBER OF SEQ ID NOS: 116

<210> SEQ ID NO 1
<211> LENGTH: 50
<212> TYPE: DNA
<213> ORGANISM: Artificial Sequence
<220> FEATURE:
<223> OTHER INFORMATION: Forward primer sequence for SARS-CoV-2 virus Spike gene

<400> SEQUENCE: 1
tctaatacct ttgctcattg acttttttc ttgttttatt gccactagtc 50

<210> SEQ ID NO 2
<211> LENGTH: 58
<212> TYPE: DNA

<213> ORGANISM: Artificial Sequence
<220> FEATURE:
<223> OTHER INFORMATION: Reverse primer sequence for SARS-COV-2 virus Spike gene

<400> SEQUENCE: 2
tacaattaat acgactcact atagggcata tttttgtcag ggtaataaac    50
accacgtg    58

<210> SEQ ID NO 3
<211> LENGTH: 50
<212> TYPE: DNA
<213> ORGANISM: Artificial Sequence
<220> FEATURE:
<223> OTHER INFORMATION: Forward primer sequence for SARS-COV-2 virus Spike gene

<400> SEQUENCE: 3
tctaatacct ttgctcattg acacctttct tttccaatgt tacttggttc    50

<210> SEQ ID NO 4
<211> LENGTH: 58
<212> TYPE: DNA
<213> ORGANISM: Artificial Sequence
<220> FEATURE:
<223> OTHER INFORMATION: Reverse primer sequence for SARS-COV-2 virus Spike gene

<400> SEQUENCE: 4
tacaattaat acgactcact atagggcata ttttatgtta gacttctcag    50
tggaagca    58

<210> SEQ ID NO 5
<211> LENGTH: 50
<212> TYPE: DNA
<213> ORGANISM: Artificial Sequence
<220> FEATURE:
<223> OTHER INFORMATION: Forward primer sequence for SARS-COV-2 virus Spike gene

<400> SEQUENCE: 5
tctaatacct ttgctcattg actttcttat tgttaataac gctactaatg    50

<210> SEQ ID NO 6
<211> LENGTH: 58
<212> TYPE: DNA
<213> ORGANISM: Artificial Sequence
<220> FEATURE:
<223> OTHER INFORMATION: Reverse primer sequence for SARS-COV-2 virus Spike gene

<400> SEQUENCE: 6
tacaattaat acgactcact atagggcata tttcattcgc actagaataa    50
actctgaa    58

<210> SEQ ID NO 7
<211> LENGTH: 50
<212> TYPE: DNA
<213> ORGANISM: Artificial Sequence
<220> FEATURE:
<223> OTHER INFORMATION: Forward primer sequence for SARS-COV-2 virus Spike gene

```
<400> SEQUENCE: 7 tctaataacct ttgctcattg acttttaagc acacgcctat taatttagtg            50

<210> SEQ ID NO 8
<211> LENGTH: 58
<212> TYPE: DNA
<213> ORGANISM: Artificial Sequence
<220> FEATURE:
<223> OTHER INFORMATION: Reverse primer sequence for SARS-COV-2 virus
      Spike gene

<400> SEQUENCE: 8
tacaattaat acgactcact atagggcata tttccacata ataagctgca            50
gcaccagc                                                          58

<210> SEQ ID NO 9
<211> LENGTH: 47
<212> TYPE: DNA
<213> ORGANISM: Artificial Sequence
<220> FEATURE:
<223> OTHER INFORMATION: Forward primer sequence for SARS-COV-2 virus
      Spike gene

<400> SEQUENCE: 9 tctaataacct ttgctcattg actgtaatta gaggtgatga agtcaga              47

<210> SEQ ID NO 10
<211> LENGTH: 58
<212> TYPE: DNA
<213> ORGANISM: Artificial Sequence
<220> FEATURE:
<223> OTHER INFORMATION: Reverse primer sequence for SARS-COV-2 virus
      Spike gene

<400> SEQUENCE: 10
tacaattaat acgactcact atagggcata tttaaaggtt tgagattaga            50
cttcctaa                                                          58

<210> SEQ ID NO 11
<211> LENGTH: 50
<212> TYPE: DNA
<213> ORGANISM: Artificial Sequence
<220> FEATURE:
<223> OTHER INFORMATION: Forward primer sequence for SARS-COV-2 virus
      Spike gene

<400> SEQUENCE: 11 tctaataacct ttgctcattg actttttattt caactgaaat ytatcaggcc          50

<210> SEQ ID NO 12
<211> LENGTH: 58
<212> TYPE: DNA
<213> ORGANISM: Artificial Sequence
<220> FEATURE:
<223> OTHER INFORMATION: Reverse primer sequence for SARS-COV-2 virus
      Spike gene

<400> SEQUENCE: 12
tacaattaat acgactcact atagggcata tttaaagtac tactactctg            50
tatggttg                                                          58

<210> SEQ ID NO 13
<211> LENGTH: 50
```

```
<212> TYPE: DNA
<213> ORGANISM: Artificial Sequence
<220> FEATURE:
<223> OTHER INFORMATION: Forward primer sequence for SARS-COV-2 virus
      Spike gene

<400> SEQUENCE: 13
tctaataccT tgctcattg actttagtgt tataacacca ggaacaaata           50

<210> SEQ ID NO 14
<211> LENGTH: 58
<212> TYPE: DNA
<213> ORGANISM: Artificial Sequence
<220> FEATURE:
<223> OTHER INFORMATION: Reverse primer sequence for SARS-COV-2 virus
      Spike gene

<400> SEQUENCE: 14
tacaattaat acgactcact atagggcata ttttgcatga atagcaacag           50
ggacttct                                                        58

<210> SEQ ID NO 15
<211> LENGTH: 50
<212> TYPE: DNA
<213> ORGANISM: Artificial Sequence
<220> FEATURE:
<223> OTHER INFORMATION: Forward primer sequence for SARS-COV-2 virus
      Spike gene

<400> SEQUENCE: 15
tctaataccT tgctcattg actttTgcag gtatatgcgc tagttatcag           50

<210> SEQ ID NO 16
<211> LENGTH: 58
<212> TYPE: DNA
<213> ORGANISM: Artificial Sequence
<220> FEATURE:
<223> OTHER INFORMATION: Reverse primer sequence for SARS-COV-2 virus
      Spike gene

<400> SEQUENCE: 16
tacaattaat acgactcact atagggcata ttttggtatg gcaatagagt           50
tattagag                                                        58

<210> SEQ ID NO 17
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 17
tttttctagt ctctaktcag tgtgtttttt                                30

<210> SEQ ID NO 18
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 18
tttttttgtc tctagtcagt gttttttttt                                30
```

<210> SEQ ID NO 19
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 19
tttttttagt ctctattcag tgtttttttt                                    30

<210> SEQ ID NO 20
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 20 tttttttaaty ttacaamcag aactcttttt                                   30

<210> SEQ ID NO 21
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 21
tttttttatc ttacaaccag aacctttttt                                    30

<210> SEQ ID NO 22
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 22
tttttttatc ttacaaccag aactttttt                                     30

<210> SEQ ID NO 23
<211> LENGTH: 32
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 23
tttttcccat gctatacatg tctctgtttt tt                                 32

<210> SEQ ID NO 24
<211> LENGTH: 32
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 24 ttttttttc catgctatct ctgggatttt tt                                  32

```
<210> SEQ ID NO 25
<211> LENGTH: 32
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 25
tttttcagag gtttgmtaac cctgtcttttt tt                                     32

<210> SEQ ID NO 26
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 26
tttttttggt ttgataaccc tgcttttttt                                         30

<210> SEQ ID NO 27
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 27
tttttttggt ttgctaaccc tgcttttttt                                         30

<210> SEQ ID NO 28
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 28
ttttattttg taatkatcca ttttttgtttt                                        30

<210> SEQ ID NO 29
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 29
tttttctttg taatgatcca ttttcttttt                                         30

<210> SEQ ID NO 30
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 30
tttttttttg taattatcca ttttcttttt                                         30

<210> SEQ ID NO 31
```

```
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 31
tttttagttg katggaaagt gagttctttt                                      30

<210> SEQ ID NO 32
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 32
tttctctaaa agttggatgg aaactcttct                                      30

<210> SEQ ID NO 33
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 33
tttcttcaaa gttgtatgga aagccttctt                                      30

<210> SEQ ID NO 34
<211> LENGTH: 32
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 34
ttttttttca aactttactt gctttactct tt                                   32

<210> SEQ ID NO 35
<211> LENGTH: 32
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 35
ttttttttca aactttacat agaagccttt tt                                   32

<210> SEQ ID NO 36
<211> LENGTH: 32
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 36
ttttctacat agaagttatt tgactcccctt tt                                  32

<210> SEQ ID NO 37
<211> LENGTH: 32
```

<210> SEQ ID NO 37
<211> LENGTH: 32
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 37
ttttctacat agaagttatt tgactcccgtt tt                                     32

<210> SEQ ID NO 38
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 38
tttctactcc tggtgrttct tcttcatttt                                         30

<210> SEQ ID NO 39
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 39 tttttttccct ggtgattctt ctttctttt                                         30

<210> SEQ ID NO 40
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 40 tttttttccct ggtggttctt ctttttttt                                         30

<210> SEQ ID NO 41
<211> LENGTH: 32
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 41
tttttaattc taamaakctt gattctaatt tt                                      32

<210> SEQ ID NO 42
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 42
tttttaattc taacaatctt gatttctttt                                         30

<210> SEQ ID NO 43
<211> LENGTH: 30
<212> TYPE: DNA

```
<213> ORGANISM: Artificial Sequence
<220> FEATURE:
<223> OTHER INFORMATION: Hybridization probe sequence for SARS-COV-2
      virus detection

<400> SEQUENCE: 43 tttttttattc taacaagctt gattttttttt                                30

<210> SEQ ID NO 44
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 44
ttttctattc taaaaatctt gatttctttt                                  30

<210> SEQ ID NO 45
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 45
tttctataat tacctgtata gattgtcttt                                  30

<210> SEQ ID NO 46
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 46 ttttttttaat tacctgtata gatttctttt                                 30

<210> SEQ ID NO 47
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 47
tttttcataa ttactggtat agatctttt                                   30

<210> SEQ ID NO 48
<211> LENGTH: 30
<212> TYPE: DNA
<213> ORGANISM: Artificial Sequence
<220> FEATURE:
<223> OTHER INFORMATION: Probe sequence for SARS-COV-2 virus detection

<400> SEQUENCE: 48 tttttttcgcc ggtagcacac ctctttttttt                                30

<210> SEQ ID NO 49
<211> LENGTH: 30
<212> TYPE: DNA
<213> ORGANISM: Artificial Sequence
<220> FEATURE:
```

```
<223> OTHER INFORMATION: Hybridization probe sequence for SARS-COV-2
      virus detection

<400> SEQUENCE: 49
ttttcttccg gtaacacacc tttttttttt                                      30

<210> SEQ ID NO 50
<211> LENGTH: 32
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 50 tttttttaatg gtgttraagg ttttaattttt tt                                 32

<210> SEQ ID NO 51
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 51 tttttttctgg tgttgaaggt tttactttttt                                    30

<210> SEQ ID NO 52
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 52
tttttttatg gtgttaaagg ttttcttttt                                      30

<210> SEQ ID NO 53
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 53
tttttttatg gtgctgaagg ttctttttttt                                     30

<210> SEQ ID NO 54
<211> LENGTH: 33
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 54 tttttttttcc aacccactwa tggtgttttt ttt                                 33

<210> SEQ ID NO 55
<211> LENGTH: 30
<212> TYPE: DNA
<213> ORGANISM: Artificial Sequence
```

```
<220> FEATURE:
<223> OTHER INFORMATION: Hybridization probe sequence for SARS-COV-2
      virus detection

<400> SEQUENCE: 55 tttttttttac ccactaatgg tgtcttttt                                        30

<210> SEQ ID NO 56
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 56 tttttttttac ccacttatgg tgtcttttt                                        30

<210> SEQ ID NO 57
<211> LENGTH: 32
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 57 tttttttatca gactcmgact aattctcttt tt                                    32

<210> SEQ ID NO 58
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 58 tttttttccag actcagacta atttctttt                                        30

<210> SEQ ID NO 59
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 59
tttttcttca gactccgact aatcttttt                                         30

<210> SEQ ID NO 60
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 60 tttttttccag actcatacta atttctttt                                        30

<210> SEQ ID NO 61
<211> LENGTH: 30
<212> TYPE: DNA
<213> ORGANISM: Artificial Sequence
<220> FEATURE:
```

```
<223> OTHER INFORMATION: Hybridization probe sequence for SARS-COV-2
      virus detection

<400> SEQUENCE: 61 tttttttccag actcacacta atttcttttt                                    30

<210> SEQ ID NO 62
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 62 tttttttcaga ctaattctcm tcggctttttt                                   30

<210> SEQ ID NO 63
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 63
tttttttcta attctcctcg gcgtttttt                                      30

<210> SEQ ID NO 64
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 64 tttttttta attctcatcg gcgtttttt                                       30

<210> SEQ ID NO 65
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 65
ttttcacttg gtgyagaaaa ttcagttttt                                     30

<210> SEQ ID NO 66
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 66
tcttcttctt ggtgcagaaa attattcttt                                     30

<210> SEQ ID NO 67
<211> LENGTH: 30
<212> TYPE: DNA
<213> ORGANISM: Artificial Sequence
```

```
<220> FEATURE:
<223> OTHER INFORMATION: Hybridization probe sequence for SARS-COV-2
      virus detection

<400> SEQUENCE: 67
tcttcttctt ggtgtagaaa attattcttt                                    30

<210> SEQ ID NO 68
<211> LENGTH: 28
<212> TYPE: DNA
<213> ORGANISM: Artificial Sequence
<220> FEATURE:
<223> OTHER INFORMATION: T7 promoter sequence on each forward primer

<400> SEQUENCE: 68
ttttctaata cctttgctca ttgactttt                                     28

<210> SEQ ID NO 69
<211> LENGTH: 19
<212> TYPE: DNA
<213> ORGANISM: Artificial Sequence
<220> FEATURE:
<223> OTHER INFORMATION: Detector probe binding nucleotide sequence
      complementary to to fluorescent labeled detect probe sequence on
      each reverse primer

<400> SEQUENCE: 69
taatacgact cactatagg                                                19

<210> SEQ ID NO 70
<211> LENGTH: 6
<212> TYPE: DNA
<213> ORGANISM: Artificial Sequence
<220> FEATURE:
<223> OTHER INFORMATION: Spacer sequence flanking the T7 promoter
      sequence in forward primer sequences

<400> SEQUENCE: 70 tacaat                                                              6

<210> SEQ ID NO 71
<211> LENGTH: 5
<212> TYPE: DNA
<213> ORGANISM: Artificial Sequence
<220> FEATURE:
<223> OTHER INFORMATION: Spacer sequence flanking the T7 promoter
      sequence in forward primer sequences

<400> SEQUENCE: 71 gcata                                                               5

<210> SEQ ID NO 72
<211> LENGTH: 50
<212> TYPE: DNA
<213> ORGANISM: Artificial Sequence
<220> FEATURE:
<223> OTHER INFORMATION: Forward primer sequence for SARS-COV-2 virus

<400> SEQUENCE: 72
ttttaatcgg tgctcttgac caaattgcaa tcttgattct aaggttggtg              50

<210> SEQ ID NO 73
<211> LENGTH: 55
<212> TYPE: DNA
<213> ORGANISM: Artificial Sequence
```

<220> FEATURE:
<223> OTHER INFORMATION: Reverse primer sequence for SARS-COV-2 virus

<400> SEQUENCE: 73
gaatttaata cgactcacta tagggataat aaagtactac tactctgtat      50
ggttg                                                       55

<210> SEQ ID NO 74
<211> LENGTH: 29
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 74
tttctataat taccdgtata gattgctttt                            29

<210> SEQ ID NO 75
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 75 ttttttttaat tacctgtata gatttctttt                           30

<210> SEQ ID NO 76
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 76
tttttcataa ttaccggtat agatctttt                             30

<210> SEQ ID NO 77
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 77
ttttttttaa ttaccagtat agactttttt                            30

<210> SEQ ID NO 78
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 78
tttttcgccg gtarcamacc ttgtatttt                             30

<210> SEQ ID NO 79
<211> LENGTH: 30
<212> TYPE: DNA
<213> ORGANISM: Artificial Sequence

```
<220> FEATURE:
<223> OTHER INFORMATION: Hybridization probe sequence for SARS-COV-2
      virus detection

<400> SEQUENCE: 79
tttttcggta gcamaccttg taatgttttt                                          30

<210> SEQ ID NO 80
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 80 ttttttggt agcacacctt gttttttttt                                           30

<210> SEQ ID NO 81
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 81 ttttttgta gcaaaccttg tatttttttt                                           30

<210> SEQ ID NO 82
<211> LENGTH: 27
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 82
taatggtgyt rmaggtttta atttttt                                             27

<210> SEQ ID NO 83
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 83 tttttctgg tgttgaaggt tttacttttt                                           30

<210> SEQ ID NO 84
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 84
tttttttatg gtgttaaagg ttttcttttt                                          30

<210> SEQ ID NO 85
<211> LENGTH: 30
<212> TYPE: DNA
<213> ORGANISM: Artificial Sequence
<220> FEATURE:
```

<223> OTHER INFORMATION: Hybridization probe sequence for SARS-COV-2
      virus detection

<400> SEQUENCE: 85
tttttttatg gtgctgaagg ttctttttt                                      30

<210> SEQ ID NO 86
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 86 tttttcggt gttgcaggtt ttatctttt                                       30

<210> SEQ ID NO 87
<211> LENGTH: 32
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 87
ttttctaatt gttactytcc tttacaattt tt                                  32

<210> SEQ ID NO 88
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 88
tttttttttg ttactttcct ttactttttt                                     30

<210> SEQ ID NO 89
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 89
tttttttttg ttactctcct ttactttttt                                     30

<210> SEQ ID NO 90
<211> LENGTH: 26
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 90
tcctttacaa ycatatggtt tttttt                                         26

<210> SEQ ID NO 91
<211> LENGTH: 24
<212> TYPE: DNA
<213> ORGANISM: Artificial Sequence

```
<220> FEATURE:
<223> OTHER INFORMATION: Hybridization probe sequence for SARS-COV-2
      virus detection

<400> SEQUENCE: 91
ttacgatcat atagtttcct tttt                                          24

<210> SEQ ID NO 92
<211> LENGTH: 23
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 92
ctttacaatc atatggtctt ttt                                           23

<210> SEQ ID NO 93
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 93
tttttctctt tacaaccata tggtcttttt                                    30

<210> SEQ ID NO 94
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 94
tttttcttac gatcatatag tttctttttt                                    30

<210> SEQ ID NO 95
<211> LENGTH: 33
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 95
ttttttttcc aacccactwa tggtgttttt ttt                                33

<210> SEQ ID NO 96
<211> LENGTH: 30
<212> TYPE: DNA
<213> ORGANISM: Artificial Sequence
<220> FEATURE:
<223> OTHER INFORMATION: Hybridization probe sequence for SARS-COV-2
      virus detection

<400> SEQUENCE: 96
ttttttttac ccactaatgg tgtctttttt                                    30

<210> SEQ ID NO 97
<211> LENGTH: 30
<212> TYPE: DNA
<213> ORGANISM: Artificial Sequence
<220> FEATURE:
```

-continued

<223> OTHER INFORMATION: Hybridization probe sequence for SARS-COV-2
      virus detection

<400> SEQUENCE: 97 tttttttttac ccacttatgg tgtctttttt                                    30

<210> SEQ ID NO 98
<211> LENGTH: 27
<212> TYPE: DNA
<213> ORGANISM: Artificial Sequence
<220> FEATURE:
<223> OTHER INFORMATION: Detector probe sequence for SARS-COV-2 virus
      detection
<220> FEATURE:
<221> NAME/KEY: modified_base
<222> LOCATION: 1
<223> OTHER INFORMATION: Thymidine at position 1 is biotinylated

<400> SEQUENCE: 98
ttttaatcgg tgctcttgac caaattg                                        27

<210> SEQ ID NO 99
<211> LENGTH: 29
<212> TYPE: DNA
<213> ORGANISM: Artificial Sequence
<220> FEATURE:
<223> OTHER INFORMATION: Detector probe sequence for SARS-COV-2 virus
      detection
<220> FEATURE:
<221> NAME/KEY: modified_base
<222> LOCATION: 1
<223> OTHER INFORMATION: Thymidine at position 1 is biotinylated

<400> SEQUENCE: 99 tttttttgaga gagatatttc aactgattt                                     29

<210> SEQ ID NO 100
<211> LENGTH: 21
<212> TYPE: DNA
<213> ORGANISM: Artificial Sequence
<220> FEATURE:
<223> OTHER INFORMATION: Detector probe sequence for SARS-COV-2 virus
      detection
<220> FEATURE:
<221> NAME/KEY: modified_base
<222> LOCATION: 1
<223> OTHER INFORMATION: Thymidine at position 1 is modified with a
      fluorescent label

<400> SEQUENCE: 100
tttctaccgt actctagctt t                                              21

<210> SEQ ID NO 101
<211> LENGTH: 21
<212> TYPE: DNA
<213> ORGANISM: Artificial Sequence
<220> FEATURE:
<223> OTHER INFORMATION: Detector probe sequence for SARS-COV-2 virus
      detection
<220> FEATURE:
<221> NAME/KEY: modified_base
<222> LOCATION: 1
<223> OTHER INFORMATION: Thymidine at position 1 is modified with a
      fluorescent label

<400> SEQUENCE: 101
tttctgttga gttatccctt t                                              21

<210> SEQ ID NO 102

```
<211> LENGTH: 43
<212> TYPE: DNA
<213> ORGANISM: Artificial Sequence
<220> FEATURE:
<223> OTHER INFORMATION: Forward primer sequence for Influenza A virus

<400> SEQUENCE: 102
tttctaccgt actctagcta cttctaaccg aggtcgaaac gta                43

<210> SEQ ID NO 103
<211> LENGTH: 60
<212> TYPE: DNA
<213> ORGANISM: Artificial Sequence
<220> FEATURE:
<223> OTHER INFORMATION: Reverse primer sequence for Influenza A virus

<400> SEQUENCE: 103
gaatttaata cgactcacta tagggataac tcaacaggca ttytggacaa         50 akcgtctacg                                                     60

<210> SEQ ID NO 104
<211> LENGTH: 34
<212> TYPE: DNA
<213> ORGANISM: Artificial Sequence
<220> FEATURE:
<223> OTHER INFORMATION: Hybridization probe sequence for Influenza A
      virus detection

<400> SEQUENCE: 104
tttttcgtgc ccagtgagcg aggactgcat tttt                          34

<210> SEQ ID NO 105
<211> LENGTH: 42
<212> TYPE: DNA
<213> ORGANISM: Artificial Sequence
<220> FEATURE:
<223> OTHER INFORMATION: Forward primer sequence for Influenza B virus

<400> SEQUENCE: 105
tttctaccgt actctagcta tcctcaactc actcttcgag cg                 42

<210> SEQ ID NO 106
<211> LENGTH: 60
<212> TYPE: DNA
<213> ORGANISM: Artificial Sequence
<220> FEATURE:
<223> OTHER INFORMATION: Reverse primer sequence for Influenza B virus

<400> SEQUENCE: 106
gaatttaata cgactcacta tagggataac tcaacagatc ggtgctcttg         50
accaaattgg                                                     60

<210> SEQ ID NO 107
<211> LENGTH: 36
<212> TYPE: DNA
<213> ORGANISM: Artificial Sequence
<220> FEATURE:
<223> OTHER INFORMATION: Hybridization probe sequence for Influenza B
      virus detection

<400> SEQUENCE: 107
ttttccaatt cgagcagctg aaactgcggt gttttt                        36

<210> SEQ ID NO 108
<211> LENGTH: 21
```

```
<212> TYPE: DNA
<213> ORGANISM: Artificial Sequence
<220> FEATURE:
<223> OTHER INFORMATION: Detector probe sequence for Influenza A and
      Influenza B virus and human Beta-2-microglobuline gene detection
<220> FEATURE:
<221> NAME/KEY: modified_base
<222> LOCATION: 21
<223> OTHER INFORMATION: Thymidine at position 21 is biotinylated

<400> SEQUENCE: 108
tttctaccgt actctagctt t                                              21

<210> SEQ ID NO 109
<211> LENGTH: 21
<212> TYPE: DNA
<213> ORGANISM: Artificial Sequence
<220> FEATURE:
<223> OTHER INFORMATION: Detector probe sequence for Influenza A and
      Influenza B virus and human Beta-2-microglobuline gene detection
<220> FEATURE:
<221> NAME/KEY: modified_base
<222> LOCATION: 21
<223> OTHER INFORMATION: Thymidine at position 21 is biotinylated

<400> SEQUENCE: 109
tttctgttga gttatccctt t                                              21

<210> SEQ ID NO 110
<211> LENGTH: 41
<212> TYPE: DNA
<213> ORGANISM: Artificial Sequence
<220> FEATURE:
<223> OTHER INFORMATION: Forward primer for human Beta-2-microglobulin
      gene

<400> SEQUENCE: 110
tttctaccgt actctagctg cctgccgtgt gaaccatgtg a                        41

<210> SEQ ID NO 111
<211> LENGTH: 60
<212> TYPE: DNA
<213> ORGANISM: Artificial Sequence
<220> FEATURE:
<223> OTHER INFORMATION: Reverse primer for human Beta-2-microglobulin
      gene

<400> SEQUENCE: 111
aatttaatac gactcactat agggataact caacagtgga attcatccaa               50
tccaaatgcg                                                           60

<210> SEQ ID NO 112
<211> LENGTH: 30
<212> TYPE: DNA
<213> ORGANISM: Artificial Sequence
<220> FEATURE:
<223> OTHER INFORMATION: Hybridization probe sequence for human
      Beta-2-microglobulin RNA detection

<400> SEQUENCE: 112
tttttagcat catggaggtt tgaagttttt                                     30

<210> SEQ ID NO 113
<211> LENGTH: 20
<212> TYPE: DNA
<213> ORGANISM: Artificial Sequence
```

```
<220> FEATURE:
<223> OTHER INFORMATION: Primer sequence for Listeria species ribosomal
      RNA analysis

<400> SEQUENCE: 113
cacactggra ctgagacacg                                                 20

<210> SEQ ID NO 114
<211> LENGTH: 21
<212> TYPE: DNA
<213> ORGANISM: Artificial Sequence
<220> FEATURE:
<223> OTHER INFORMATION: Primer sequence for Listeria species ribosomal
      RNA analysis

<400> SEQUENCE: 114
gtattaccgc ggctgctggc a                                               21

<210> SEQ ID NO 115
<211> LENGTH: 40
<212> TYPE: DNA
<213> ORGANISM: Artificial Sequence
<220> FEATURE:
<223> OTHER INFORMATION: Primer sequence for Listeria species ribosomal
      RNA analysis

<400> SEQUENCE: 115
tttctaccgt actctagcta cacactggra ctgagacacg                           40

<210> SEQ ID NO 116
<211> LENGTH: 58
<212> TYPE: DNA
<213> ORGANISM: Artificial Sequence
<220> FEATURE:
<223> OTHER INFORMATION: Primer sequence for Listeria species ribosomal
      RNA analysis

<400> SEQUENCE: 116
gaatttaata cgactcacta tagggataac tcaacaggta ttaccgcggc                50
tgctggca                                                              58
```

TRANSCRIPTION MEDIATED AMPLIFICATION METHODS FOR RNA DETECTION

CROSS-REFERENCE TO RELATED APPLICATIONS

This non-provisional application claims benefit of priority under 35 U.S.C. 119(e) of provisional application U.S. Ser. No. 63/210,934, filed Jun. 15, 2021, the entirety of which is hereby incorporated by reference.

BACKGROUND OF THE INVENTION

Field of the Invention

The present invention relates to the field of multiplex-based pathogen detection and analysis. More particularly, the present invention relates to combining isothermal amplification methods with microarray technology for detecting the presence of an RNA in pathogens, plants, animals, humans and the environment.

Description of the Related Art

PCR technology has dominated diagnostics and public health screening during pandemics. Independent of the test developer, PCR has been shown to have an unusually high false negative rate (15% up to 30%). Meta-analysis has shown that the false negative rate for PCR is high when pathogen load is low. This renders traditional PCR ineffective as a tool for early detection of weak symptomatic carriers while also lessening its value in epidemiology. Moreover, traditional PCR is unable to meet the increasing demand for rapid point-of-care and field testing, which are crucial for management of diseases during pandemics.

It is well known in the art that DNA and RNA analytes may be enzymatically amplified to prior to analysis by hybridization to cognate nucleic acid probes. Such amplification methods include thermal cycling (PCR) and a number of reactions which are not based on thermal cycling and thus as a class are referred to as "Isothermal". These include loop-assisted isothermal amplification (LAMP) and Recombinase Polymerase Amplification (RPA), which generate amplified DNA fragments, and isothermal amplification methods including Transcription Mediated Amplification (TMA) especially the NASBA variant of TMA, "TMA (NASBA)" which generate amplified RNA fragments. A known limitation of these isothermal methods is the difficulty to introduce dyes or other markers and tags into the amplified nucleic acid fragments. This is particularly difficult with conventional TMA methods, where the amplification reaction produces single stranded RNA amplicons.

Thus, conventional PCR amplification and detection methods are unsuitable for rapid point-of-care and field testing due to stringent temperature-controlled assay requirements. Thus, there is a need in the art for improved multiplex RNA analysis previously attainable only by Next Generation Sequencing in a highly specialized environment. The present invention fulfills this long-standing need and desire in the art.

SUMMARY OF THE INVENTION

The present invention is directed to a method for detecting a COVID-19 virus in a sample. In the method a sample is obtained and crude nucleic acids are isolated therefrom. A combined isothermal reverse transcription, RNAse H and isothermal amplification reaction is performed on the crude nucleic acids using a plurality of forward primers each with an RNA polymerase promoter sequence or the RNA polymerase promoter sequence and a detector probe nucleotide sequence at its 5' end and a plurality of reverse primers each comprising a fluorescent labeled detector probe nucleotide sequence at its 5' end to generate a plurality of single stranded RNA amplicons each with a sequence complementary to the fluorescent labeled detector probe nucleotide sequence at the 5' end, the 3' end or a combination thereof of each of the plurality of RNA amplicons. The RNA amplicons are hybridized at an ambient temperature on a microarray support with a plurality of the fluorescent labeled detector probes, and a plurality of hybridization probes with sequences complementary to a sequence determinant in the COVID-19 virus. The microarray is washed and imaged to detect at least one fluorescent signal from at least one of the plurality of fluorescent labeled detector probes thereby detecting the presence of the COVID-19 virus in the sample. The present invention is directed to a related method further comprising isolating total RNA or mRNA from the crude nucleic acids and performing the combined isothermal reverse transcription, RNAse H and isothermal RNA amplification reaction on the total RNA. The present invention is directed to another related method comprising calculating an intensity of the fluorescent signal to correlate with a copy number of the COVID-19 virus in the sample.

The present invention also is directed to a method for detecting an RNA of interest in a sample. In the method nucleic acids are isolated from the sample. A combined isothermal reverse transcription and isothermal RNA amplification reaction using at least one forward primer comprising at its 5' end an RNA polymerase promoter sequence or the RNA polymerase promoter sequence and a detector probe nucleotide sequence and at least one reverse primer comprising at its 5' end a fluorescent labeled detector probe to generate single stranded RNA amplicons each comprising a sequence complementary to the fluorescent labeled detector probe nucleotide sequence. The single-stranded RNA amplicons are hybridized on a solid microarray to at least one of the fluorescent labeled detector probes and at least one hybridization probe comprising a nucleotide sequence complementary to a sequence determinant in the RNA of interest. The microarray is washed at least once and imaged to detect at least one fluorescent signal from at least one of the plurality of fluorescent labeled detector probes thereby detecting the RNA of interest in the sample. The present invention is directed to a related method further comprising calculating an intensity of the fluorescent signal to correlate with a copy number of the RNA of interest in the sample.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

These and other features, aspects, and advantages of the embodiments of the present disclosure will become better understood when the following detailed description is read with reference to the accompanying drawings in which like characters represent like parts throughout the drawing, wherein.

DETAILED DESCRIPTION OF THE INVENTION

Figure 1:
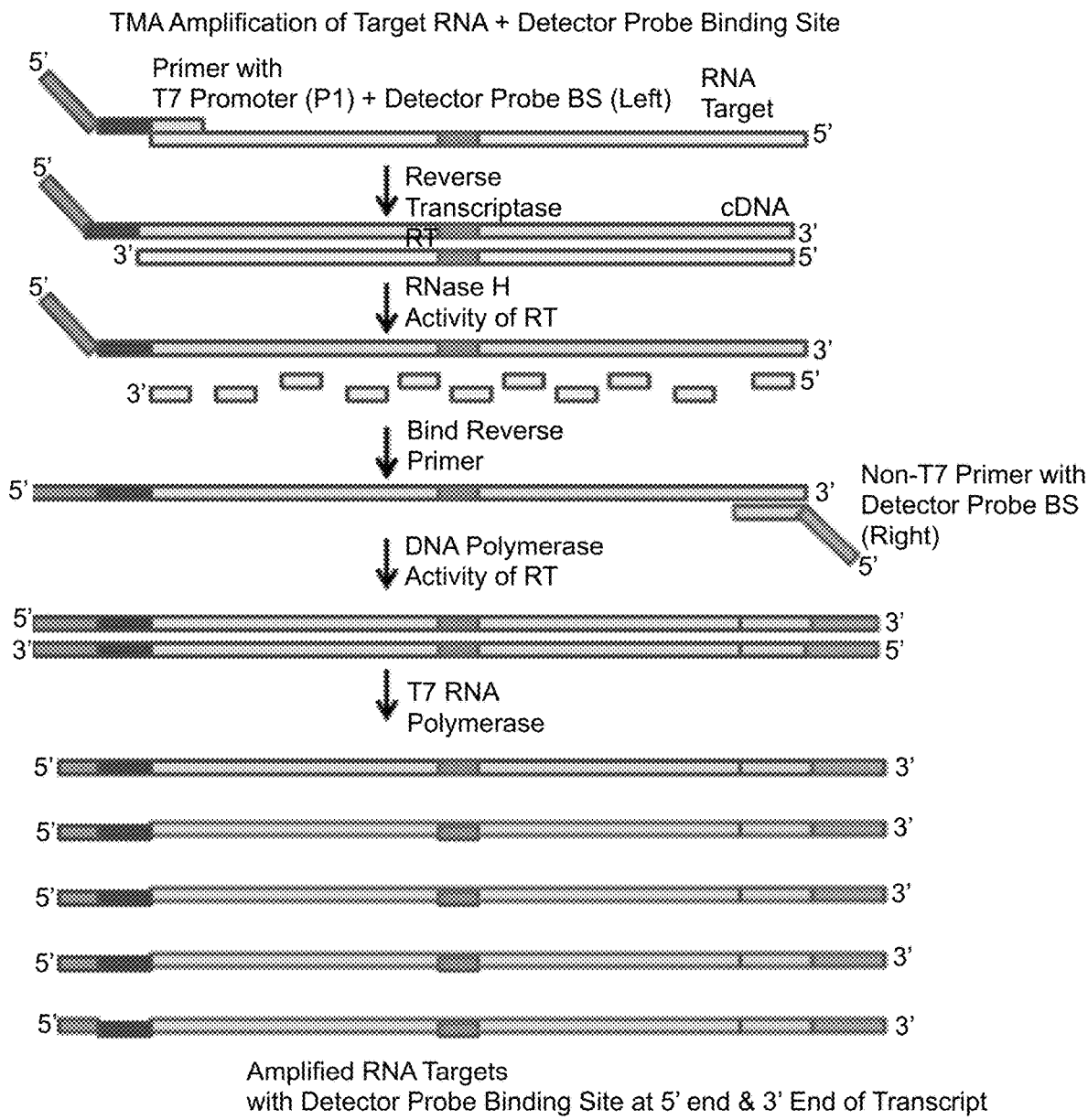
FIG. 1 illustrates the steps in nucleic acid sequence-based Transcription Mediated Amplification (TMA) of target RNA.

As used herein, the term "a" or "an" when used in conjunction with the term "comprising" in the claims and/or the specification may mean "one," but it is also consistent with the meaning of "one or more," "at least one," and "one or more than one." Some embodiments of the invention may consist of or consist essentially of one or more elements, method steps, and/or methods of the invention. It is contemplated that any method described herein can be implemented with respect to any other method described herein.

As used herein, the term "or" in the claims is used to mean "and/or" unless explicitly indicated to refer to alternatives only or the alternatives are mutually exclusive, although the disclosure supports a definition that refers to only alternatives and "and/or." As used herein, "comprise" and its variations, such as "comprises" and "comprising," will be understood to imply the inclusion of a stated item, element or step or group of items, elements, or steps but not the exclusion of any other item, element or step or group of items, elements, or steps unless the context requires otherwise. Similarly, "another" or "other" may mean at least a second or more of the same or different claim element or components thereof.

As used herein, the term "detector probe binding sequence" is a nucleotide sequence located at the 5' ends or the 3' ends of the RNA amplicons generated. The detector probe binding sequence comprises a nucleotide sequence that is complementary to a nucleotide sequence in the fluorescent labeled detector probe, which is employed to detect RNA amplicon(s) binding to the hybridization probe(s). As used herein, the term "detector probe binding complementary nucleotide sequence" refers to a sequence in the forward and or reverse primer used in amplification to generate the RNA amplicons comprising at their 3' ends, the detector probe binding sequence. Thus, the detector probe binding complementary nucleotide sequence is substantially similar to the nucleotide sequence in the fluorescent labeled detector probe.

In one embodiment of the present invention, there is provided a method for detecting a COVID-19 virus in a sample comprising obtaining the sample; isolating crude nucleic acids therefrom; performing, on the crude nucleic acids, a combined isothermal reverse transcription, RNAse H and isothermal RNA amplification reaction using a plurality of forward primers each comprising at its 5' end an RNA polymerase promoter sequence or the RNA polymerase promoter sequence and a detector probe nucleotide sequence and a plurality of reverse primers each comprising at its 5' end a fluorescent labeled detector probe nucleotide sequence to generate a plurality of single stranded RNA amplicons each comprising a sequence complementary to the fluorescent labeled detector probe nucleotide sequence at the 5' end, the 3' end or a combination thereof of each of the plurality of RNA amplicons; hybridizing, at an ambient temperature, the plurality of single-stranded RNA amplicons to a plurality of the fluorescent labeled detector probes and a plurality of hybridization probes each comprising a nucleotide sequence complementary to a sequence determinant in the COVID-19 virus, said hybridization probes attached to a solid microarray support; washing the microarray support at least once; and imaging the microarray support to detect at least one fluorescent signal from at least one of the plurality of fluorescent labeled detector probes, thereby detecting the COVID-19 virus in the sample.

Further to this embodiment, the method comprises isolating total RNA or mRNA after the lysing stem where the performing step comprises performing the combined isothermal reverse transcription, RNAse H and isothermal RNA amplification reaction on the total RNA. In another further embodiment the method comprises calculating an intensity of the fluorescent signal to correlate with a copy number of the COVID-19 virus in the sample.

In all embodiments, the COVID-19 virus in the sample is a wild type COVID-19 virus or a clade variant thereof. In a non-limiting example, the clade variant is, but not limited to, a B.1.2, B.1.1.7, B.1.351, B.1.375, B.1.427, B.1.429, B.1.525, B.1.526, P1, P2 and Wuhan. The sample may also comprise a combination of wild type COVID-19 and its clade variants in various proportions.

In all embodiments a combined isothermal reverse transcription and isothermal amplification reaction is performed on the crude nucleic acids to generate a plurality of single stranded RNA amplicons. The combined reaction is performed as a single homogenous reaction in a solution comprising a plurality of forward primers each comprising an RNA polymerase promoter sequence at its 5' ends and, optionally, a detector probe nucleotide sequence at its 5' end, a plurality of reverse primers each comprising at its 5' end, a fluorescent labeled detector probe nucleotide sequence, a reverse transcriptase, an RNase H activity, and an RNA polymerase. In this embodiment, the reverse transcriptase uses the plurality of RNA as template to generate an RNA: cDNA duplex. The RNA in the RNA:cDNA duplex is digested by the intrinsic RNase H activity of the reverse transcriptase (TMA) or an added extrinsic RNAse H activity, TMA (NASBA), to obtain a single stranded cDNA. The cDNA thus obtained is amplified (during isothermal amplification) by the intrinsic DNA polymerase activity or the reverse transcriptase to obtained cDNA duplexes, which are then transcribed by the RNA polymerase to generate a plurality of RNA amplicons corresponding to the plurality of RNA in the sample (hence, Transcription Mediated Amplification). Moreover, each of the plurality of RNA amplicons comprises a sequence complementary to the fluorescent labeled detector probe sequence.

In these embodiments, the binding of the primers suitable to drive reverse transcription is performed at a temperature of about 65° C. or greater, while the reverse transcription, RNase activity and isothermal amplification is performed at a temperature of about 40° C. Typically, the ambient temperature is below a temperature for isothermal reverse transcription and a temperature for isothermal amplification. Particularly, the hybridization step is performed at an ambient temperature between 15° C.-30° C.

In this embodiment, any RNA polymerase promoter sequence is employed. For example, in one aspect, the RNA polymerase promoter sequence is a T7 promoter sequence that would enable generation of single stranded RNA amplicons using a T7 RNA polymerase. Exemplary COVID-19 virus specific primers comprising a T7 promoter sequence are shown in Table 2 (even SEQ ID NOS.). Exemplary COVID-19 virus specific reverse primers comprising a nucleotide sequence of the fluorescent labeled detector probe are shown in Table 2 (odd SEQ ID NOS.). Particularly, the plurality of forward primers comprises the nucleotide sequences of SEQ ID NO: 1, SEQ ID NO: 3, SEQ ID NO: 5, SEQ ID NO: 7, SEQ ID NO: 9, SEQ ID NO: 11, SEQ ID NO: 13, or SEQ ID NO: 15 and the plurality of reverse primers comprises the nucleotide sequences of SEQ ID NO: 2, SEQ ID NO: 4, SEQ ID NO: 6, SEQ ID NO: 8, SEQ ID NO: 10, SEQ ID NO: 12, SEQ ID NO: 14, or SEQ ID NO: 16.

The plurality of RNA amplicons generated are hybridized on a microarray support containing a solution comprising a plurality of the fluorescent labeled detector probes and, a plurality of hybridization probes immobilized on the microarray surface. In this embodiment, each of the hybridization probes are attached at specific positions on the microarray support and have a nucleotide sequence complementary to a sequence determinant in the COVID-19 virus. Exemplary COVID-19 virus specific hybridization probes are shown in Table 3 and Table 5. Particularly, the plurality of hybridization probes comprises the nucleotide sequences of SEQ ID NOS: 17-67 or SEQ ID NOS: 74-97.

In these embodiments, the solution phase fluorescent labeled detector probes have a nucleotide sequence that is complementary to a detector probe binding sequence at the 5' ends and/or the 3' ends of each of the plurality of RNA amplicons. This enables binding of the fluorescent labeled detector probe to RNA amplicons that are hybridized to the hybridization probe, which are immobilized on the microarray support.

Thus, the fluorescent labeled detector probe enables detection of hybridized RNA amplicon(s) using a fluorescent imager. The fluorescent labeled detector probe has a base length of about 15 nucleotides to about 30 nucleotides and/or a nucleotide sequence with a GC content of about 40% to about 60%. Also in these embodiments the plurality of fluorescent labeled detector probes is in a molar ratio of about 0.1 to about 5 with the plurality of single-stranded RNA amplicons. Particularly, the fluorescent labeled detector probe nucleotide sequence comprises SEQ ID NO: 68, SEQ ID NO: 98, SEQ ID NO: 99, SEQ ID NO: 100, or SEQ ID NO: 101. Also in this embodiment, any fluorescent label may be used in the detector probe including, but not limited to, a CY3, a CYS, SYBR Green, a DYLIGHT™ DY647, an ALEXA FLUOR 647, a DYLIGHT™ DY547, an ALEXA FLUOR 550 phycoerythrin.

After hybridization, the microarray is washed at least once to remove unhybridized amplicons and unbound detector probes. Washed microarrays are imaged to detect at least one from at least one of the plurality of fluorescent labeled detector probed bound to the RNA amplicon(s), thereby detecting presence of the COVID-19 virus in the sample.

In all embodiments and aspects thereof, the sample may comprise at least one of a nasopharyngeal swab, a nasal swab, a mouth swab, a mouthwash, a biopsy sample, a blood sample, an aerosol, or a swab from a hard surface. In one aspect the sample may be any sample obtained from a subject including, but not limited to, a nasopharyngeal swab, a nasal swab, a mouth swab, and a mouthwash (sample obtained by rinsing the subject's buccal cavity). A pooled sample obtained by combining two or more of these samples or by combining samples from multiple subjects also may be used. In another aspect, the sample is an environmental sample obtain from inanimate sources including but is not limited to an aerosol and a hard surface. The aerosol samples may be obtained using commercial air samplers such as for example a Coriolis Micro Air Sampler. A sample from a hard surface may be obtained using a swab. In both aspects, the viruses from samples obtained on swabs are dispersed in a liquid such as phosphate buffered saline. Aerosol samples are transferred into a volume of a liquid such as phosphate buffered saline.

In all of the embodiments and aspects thereof, the reverse primer sequence does not comprise the promoter sequence. Also, in all of the embodiments, the isothermal reaction does not employ any nucleotide bases other than A, G, C, T and U. Further, in all embodiments, the nucleotide sequence of the detector probe has a base length from about 15 nucleotides to about 30 nucleotides. Further still in this embodiment, the nucleotide sequence in the detector probe has a GC content from about 40% to about 60%. In these embodiments the reverse transcription, isothermal amplification, hybridization and imaging steps are performed on separate workstations. Alternatively, the reverse transcription, isothermal amplification, hybridization and imaging steps are performed as sub-assemblies in an integrated device, which is advantageous since it enables full automation with minimal human intervention.

In another embodiment of the present invention, there is provided a method for detecting an RNA of interest in a sample comprising obtaining the sample; isolating nucleic acids from the sample; performing on the nucleic acids, a combined isothermal reverse transcription and isothermal RNA amplification reaction using at least one forward primer comprising at its 5' end an RNA polymerase promoter sequence or the RNA polymerase promoter sequence and a detector probe nucleotide sequence and at least one reverse primer comprising at its 5' end a fluorescent labeled detector probe to generate single stranded RNA amplicons each comprising a sequence complementary to the fluorescent labeled detector probe nucleotide sequence; hybridizing the single-stranded RNA amplicons to at least one of the fluorescent labeled detector probes and at least one hybridization probe comprising a nucleotide sequence complementary to a sequence determinant in the RNA of interest, said at least one hybridization probe attached to a solid microarray; washing the microarray at least once; and imaging the microarray to detect at least one fluorescent signal from at least one of the plurality of fluorescent labeled detector probes, thereby detecting the RNA of interest in the sample. Further to this embodiment the method comprises calculating an intensity of the fluorescent signal to correlate with a copy number of the RNA of interest in the sample.

Generally, the overall composition of the primer and probe sequences, the sequence determinants and complementary sequences and fluorescent label on the detector probe are as described supra. In both embodiments, the fluorescent labeled detector probe is in a molar ratio of about 0.1 to about 5 with the single-stranded RNA amplicons. Also in both embodiments the nucleic acids are crude nucleic acids, total RNA, mRNA, or ribosomal RNA. In addition in both embodiments the RNA of interest is a viral RNA, a bacterial RNA, or a pathogenic viral RNA, a fungal RNA or a combination thereof, or a plant RNA, an animal RNA, or a human RNA. For example, the pathogenic viral RNA is isolated from Severe Acute Respiratory Syndrome Coronavirus 2 (COVID-19 virus), a Respiratory Syncytial Virus, a Middle East Respiratory Syndrome coronavirus (MERS-CoV), a Severe Acute Respiratory Syndrome Coronavirus (SARS-CoV), a 229E Coronavirus, a OC43 Coronavirus, a NL63 Coronavirus, a HKU1 Coronavirus, an Influenza A virus, or an Influenza B virus or a combination thereof. The sample may also comprise a combination of respiratory viruses. The RNA of interest may be from a healthy tissue, or a tissue suspected of being cancerous.

In one aspect of both embodiments, the pathogenic viral RNA is isolated from a wild type COVID-19 virus or a clade variant thereof. In a non-limiting example, the clade variant is, but not limited to B.1.2, B.1.1.7, B.1.351, B.1.375, B.1.427, B.1.429, B.1.525, B.1.526, P1, P2 and Wuhan. The sample also may comprise a combination of wild type COVID-19 and its clade variants in various proportions. In this aspect the nucleotide sequences for the forward primers, the reverse primers, the fluorescent labeled detector probes, and the hybridization probes are as described supra.

In another aspect of both embodiments, the pathogenic viral RNA is isolated from an Influenza A virus. In this aspect the nucleotide sequences for the reverse primers, the fluorescent labeled detector probes, and the hybridization probes are shown in Table 5. Particularly, the forward primer comprises the nucleotide sequence of SEQ ID NO: 102 and the reverse primer comprises the nucleotide sequence of SEQ ID NO: 103. Also, the fluorescent labeled detector probe comprises the nucleotide sequence of SEQ ID NO: 108 or SEQ ID NO: 109 or a combination thereof. In addition the at least one hybridization probe comprises the nucleotide sequences of SEQ ID NO: 104.

In another aspect of both embodiments, the pathogenic viral RNA is isolated from an Influenza B virus. In this aspect the nucleotide sequences for the reverse primers, the fluorescent labeled detector probes, and the hybridization probes are shown in Table 5. Particularly, the forward primer comprises the nucleotide sequence of SEQ ID NO: 105 and the reverse primer comprises the nucleotide sequence of SEQ ID NO: 106. Also, the fluorescent labeled detector probe comprises the nucleotide sequence of SEQ ID NO: 108 or SEQ ID NO: 109 or a combination thereof. In addition the at least one hybridization probe comprises the nucleotide sequences of SEQ ID NO: 107.

In both embodiments and aspects thereof the combined isothermal reverse transcription, RNAse H and isothermal amplification reaction is performed on the nucleic acids as described supra to generate the plurality of single stranded RNA amplicons. Particularly, the temperature at which the isothermal reverse transcription and the isothermal amplification are performed, the promoter sequence and the RNA polymerase are as described supra. Also in both embodiments and aspects thereof the RNA amplicons hybridizing step and ambient temperature at which it is performed, the microarray and the attachment position of the hybridization probes thereon are as described supra. In addition the sample may comprise at least one of a nasopharyngeal swab, a nasal swab, a mouth swab, a skin swab and vaginal swab, a mouth wash, a skin wash, a plant wash, a homogenized food sample, a blood sample, a biopsy sample, an aerosol, or a hard surface swab.

Provided herein is a multiplex isothermal TMA or NASBA amplification method of several viral RNA targets and a control human RNA target concurrently followed by hybridization of those ribonucleic amplicons to surface bound nucleic acid probes comprising a microarray. Moreover, subsequent to such multiplex isothermal RNA amplification, the resulting microarray hybridization may be used to identify the presence of each individual viral RNA target in the original sample, as distinct from the human RNA control, and, where appropriate, to obtain sequence information at discrete locations within one or more of those RNA targets. The resulting local sequence information may be used to detect local genetic variation within a RNA sequence, which, in the case of viral RNA sequences, may be used to detect the presence of specific viral sequence variation which can be used to identify specific viral subtypes (i.e. variants). Particularly, a mixture of the RNA viruses SARS-CoV-2, Influenza A and Influenza B and also a human RNA amplification control (B2M) was detected where additional sequencing by hybridization was performed on a specific region of the SARS-CoV-2 genome, which in turn is used to establish which SARS-CoV-2 Variant is present in the viral mixture.

During the multiplex TMA or NASBA reaction, primer mediated isothermal amplification produces RNA amplicons which acquire Detector Probe Binding sequences which are suitable to bind fluorescently labeled Detector Probes that are introduced in the hybridization or wash buffers, thereby forming a [Hybridization Probe-RNA amplicon-Detector Probe] "Sandwich". In the present Example, the Detector Probes are DNA oligonucleotides synthesized with a biotin group at their 5' termini. When mixed with Streptavidin modified Phycoerythrin (SAPE) a SAPE-Detector Probe complex is formed, thereby labeling the RNA amplicon as bound to its cognate hybridization probe.

The following examples are given for the purpose of illustrating various embodiments of the invention and are not meant to limit the present invention in any fashion.

Example 1

Method
Transcription Mediated Amplification

FIG. 1 illustrates the general approach to amplifying a target RNA using Transcription Mediated Amplification (TMA), or alternatively the corresponding NASBA variant of TMA that is in every way identical, except that an exogenous RNAseH enzyme is added to the enzymatic reaction rather than using the endogenous RNAseH activity of Reverse Transcriptase. The TMA (NASBA) method produces an amplified RNA that is modified during the course of the combined "One Pot" enzyme reactions to include a new terminal RNA sequence ("Primer with T7 promoter", P1) or in some cases a new T7 promoter adjacent to a detector probe nucleotide sequence, either introduced as a DNA oligonucleotide primer during reverse transcription. The cDNA generated after reverse transcription is amplified using a non-T7 primer with a detector probe nucleotide sequence (15-30 bases) attached at its 5' end (FIG. 1). After completion of the combined reverse transcription/amplification reaction, the resulting double stranded cDNA is incubated with T7 RNA polymerase to generate multiple copies of single stranded RNA amplicons (FIG. 1).

Figure 2:
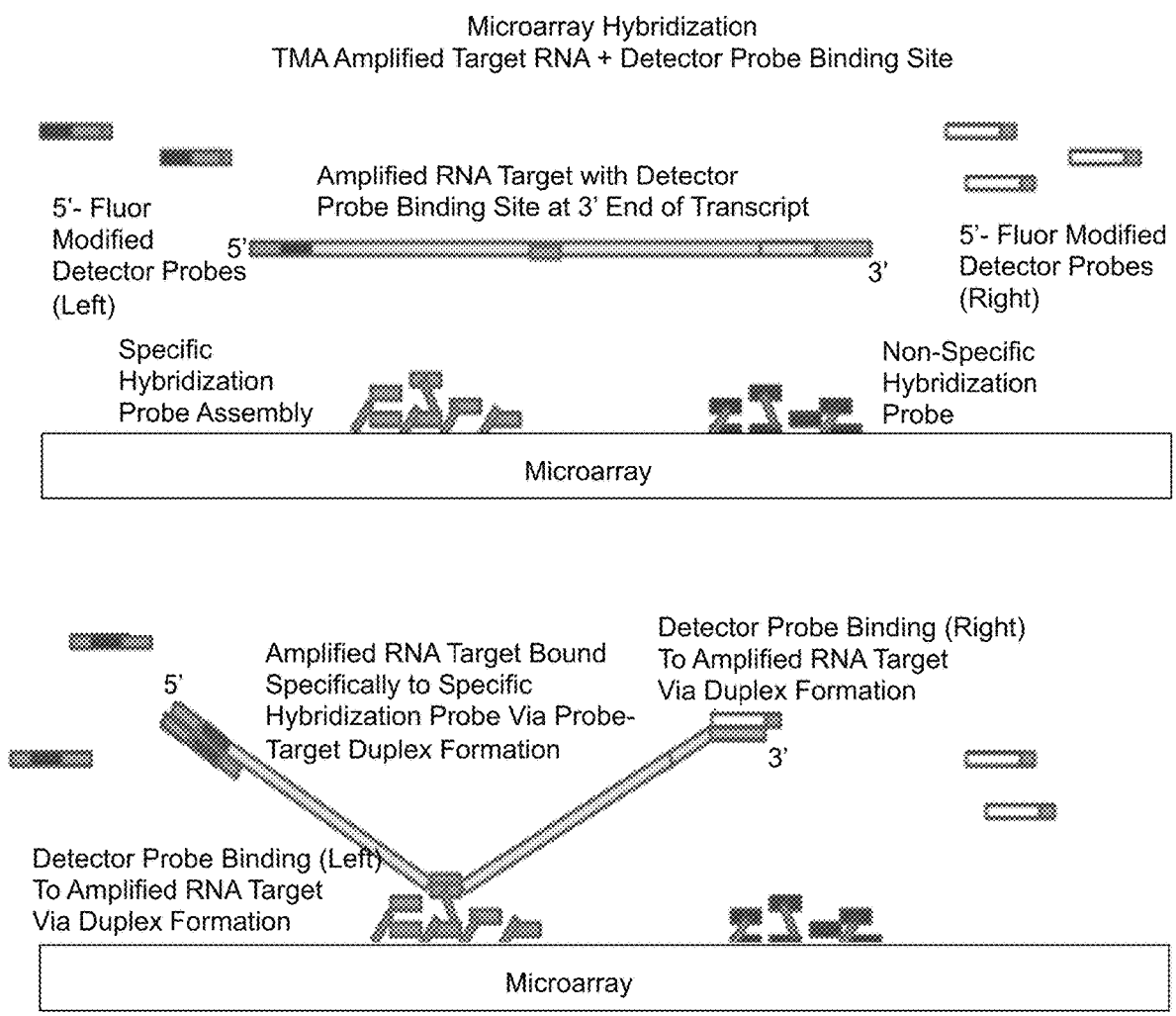
FIG. 2 illustrates hybridization of the amplified RNA target to hybridization probes on the microarray substrate.
Figure 3A:
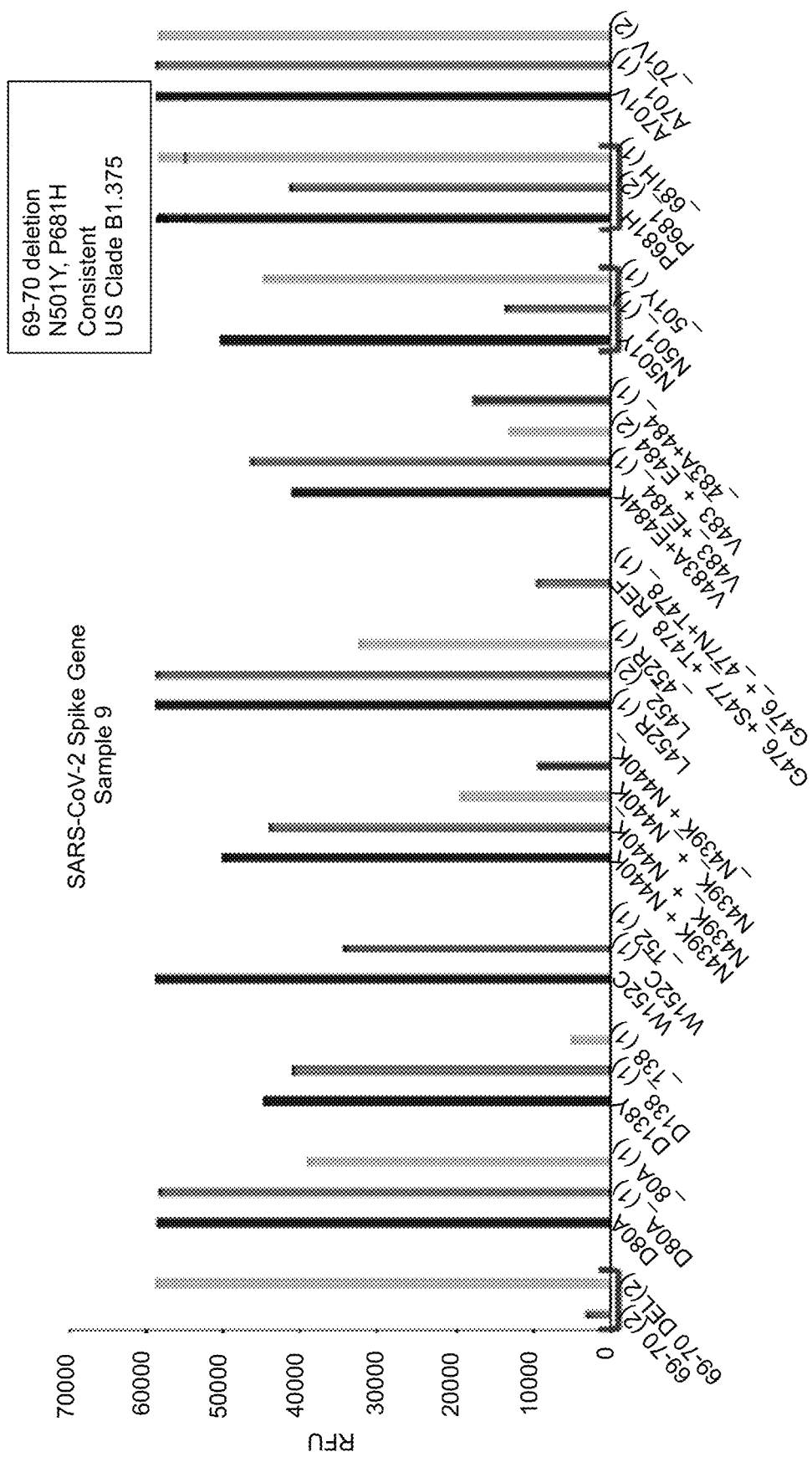
FIGS. 3A-3D show the results in identifying variants in clinical samples.
Figure 3B:
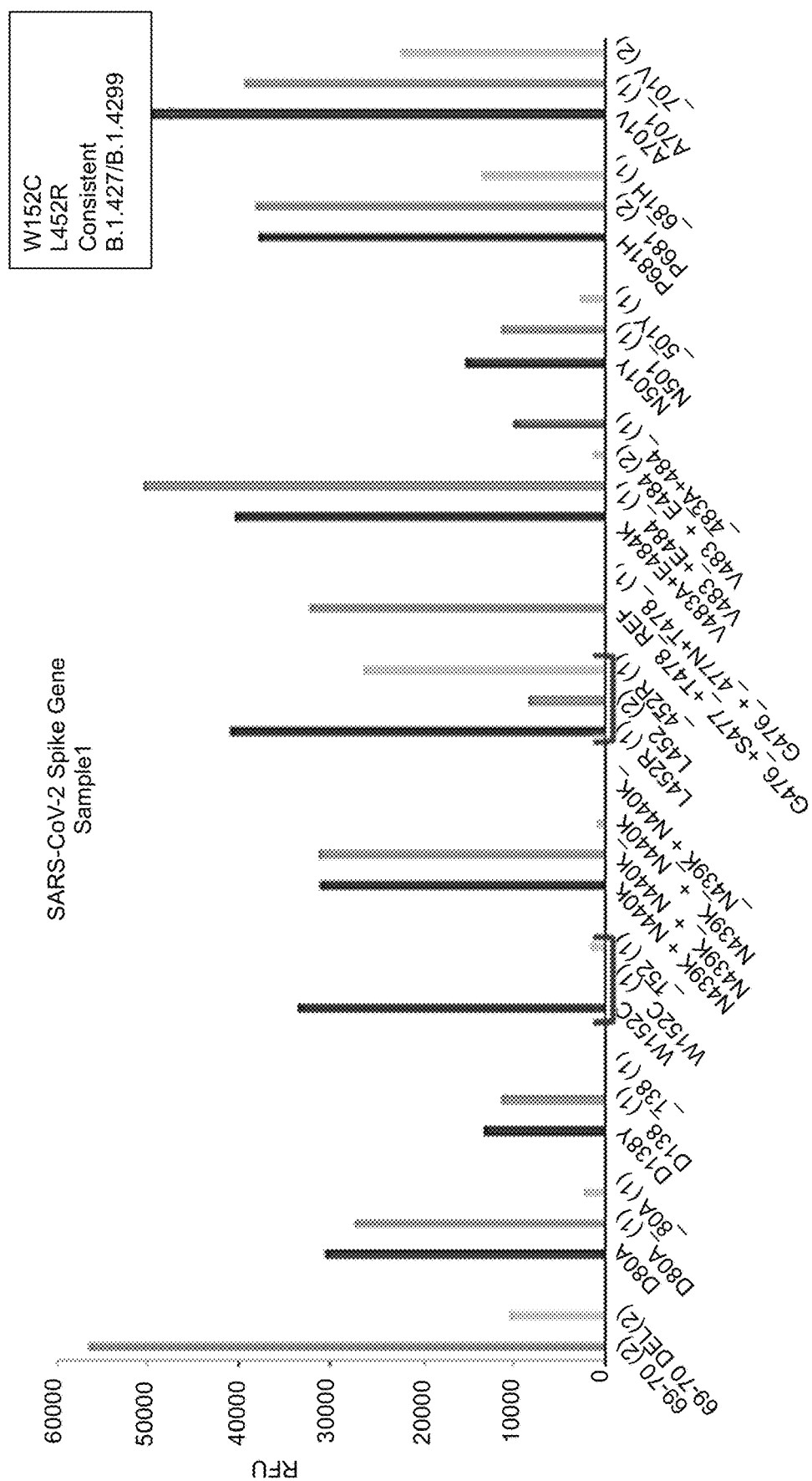
Figure 3C:
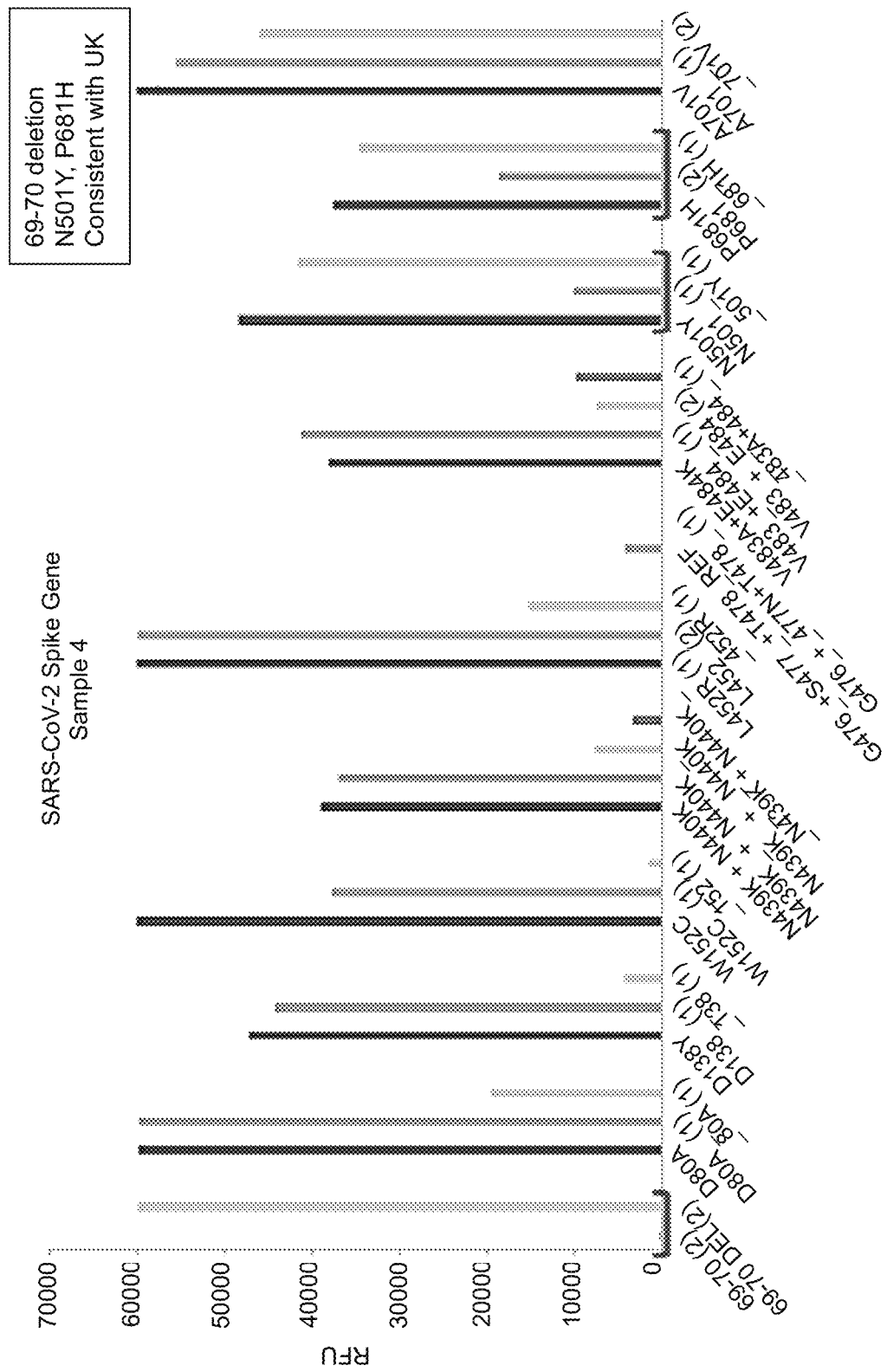
Figure 3D:
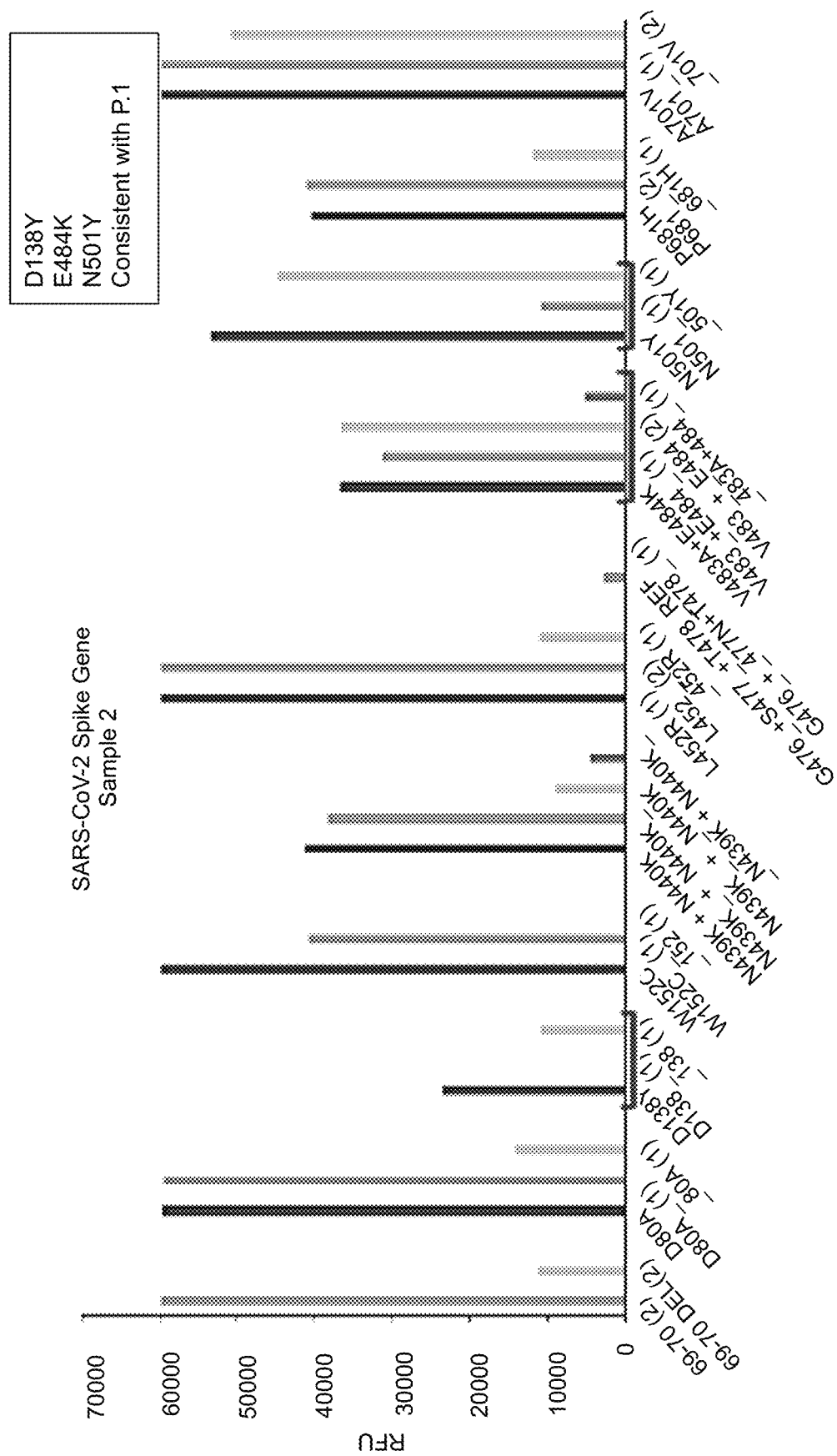
Figure 4:
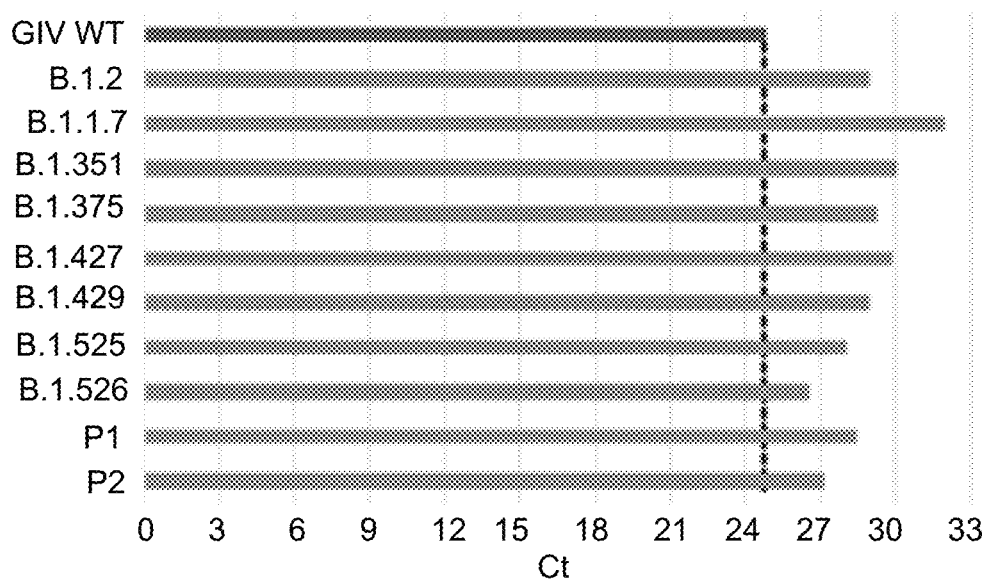
FIG. 4 is a comparison of VOC/I with GIV WT.
Figure 5:
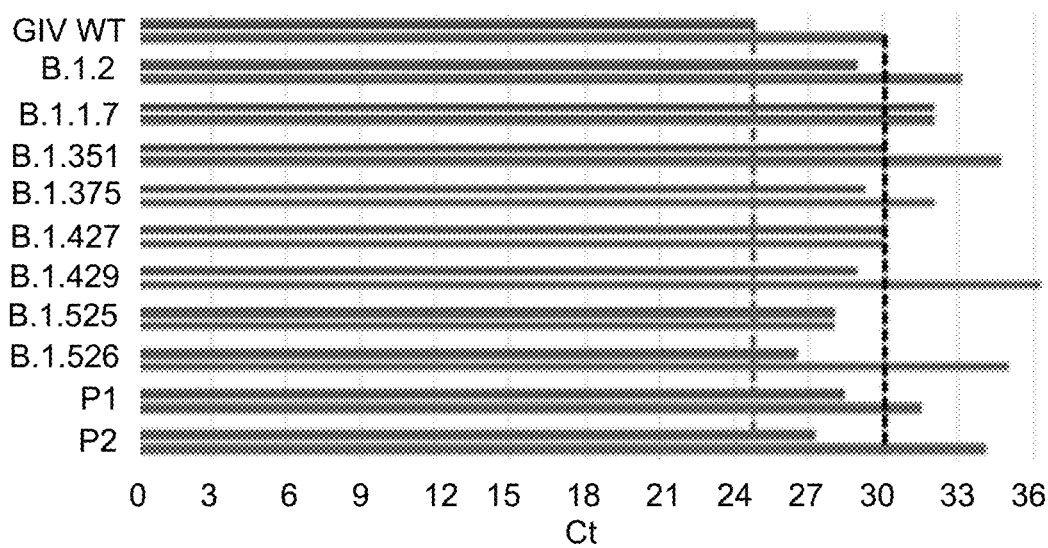
FIG. 5 is a comparison of VOC/I Cv Ct for correct variant identification vs Cv Ct to detect Cov-2 spike.
Figure 6:
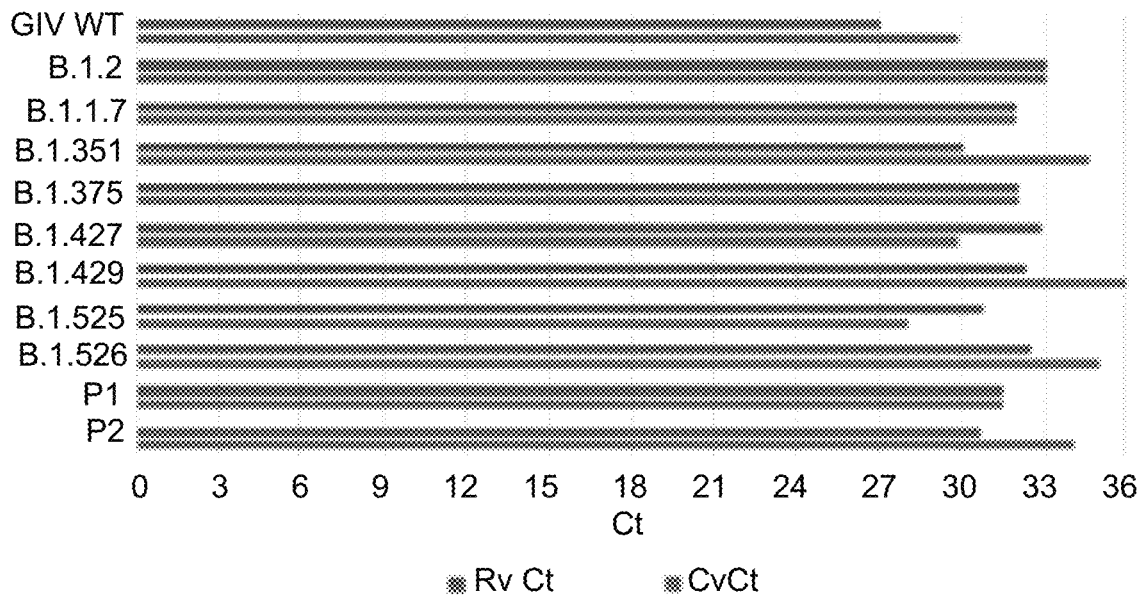
FIG. 6 is a comparison of VOC/I Rv array Ct vs the Cv Ct array ability to detect CoV-2 spike.
Figure 7:
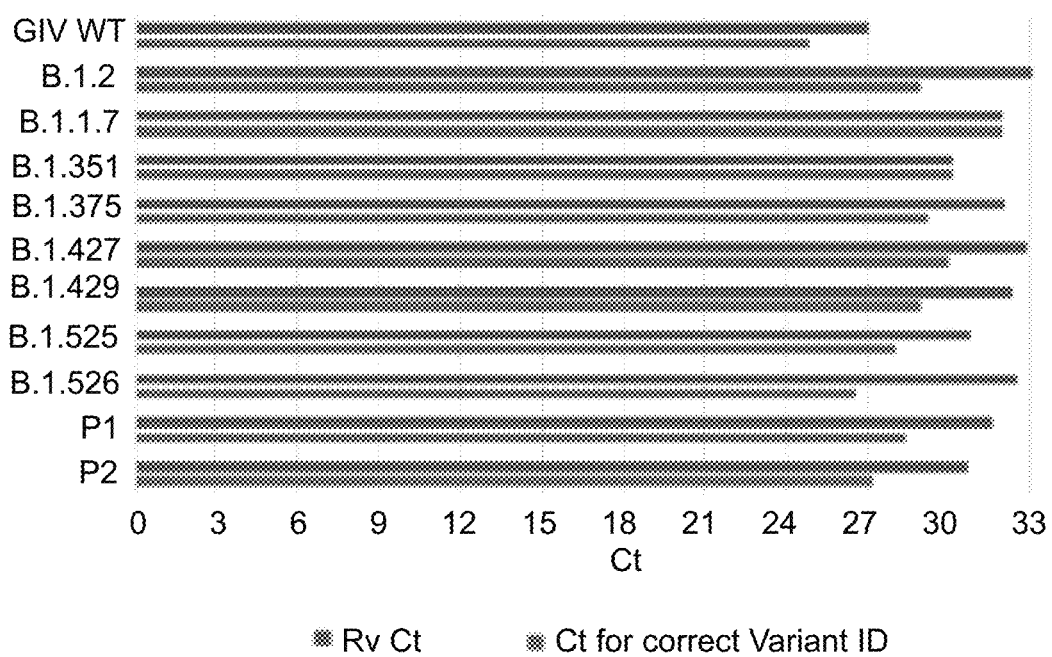
FIG. 7 is a comparison of VOC/I Rv array Ct vs the Cv array ability to correctly identify a variant.

In the present invention, surface bound oligonucleotide hybridization probes are designed with a sequence that will bind to amplified RNA (FIG. 2) at ambient temperature (15° C.-30° C.). The probes are fabricated on the microarray surface such that they are positioned away from direct contact with the underlying microarray substrate, preferably in a 3-dimensional assembly formed as shown in FIG. 2. Thus, when TMA (NASBA) amplified RNA binds to its cognate hybridization probe at ambient temperature, the bound complex is also positioned away from the microarray substrate. Upon binding of the detector probes which had been introduced as part of the hybridization or washing reactions, the 3-fold complex (hybridization probe+amplified RNA target+detector probe) comprises a "Sandwich Assay" analogous to immunoassays. The dye or chemical label introduced onto the detector probe can be for example, a fluorescent tag chemically linked to the 5' end of the detector probe or a conjugate such as phycoerthyrin-streptaviden bound non-covalently to a biotin moiety covalently linked to the 5' end of the detector probe. Either labeling approach (covalent or non-covalent) thus enabling detection of amplified RNA binding to hybridization probes at the surface.

Multiplex Analysis of Viral Contamination

A sample containing one or more viruses is collected from a human or animal subject from the airway, via a Nasopharyngeal (NP) or Anterior Nasal (AN) swab, or from saliva. The sample is dispersed in a saline solution and lysed by heating. RNA is extracted by magnetic beads or similar methods. Alternatively, the sample is analyzed directly without RNA extraction.

Concentrated TMA enzyme solution is added to the extracted RNA or lysed solution and amplified as a two-step isothermal reaction, once at 65° C. for about 5 min and then once at 41° C. for about 10 min to about 60 min to produce "n" different amplified RNAs, to be analyzed, as one set on a DNA microarray hybridization device. The amplified product is used as-is by adding a binding buffer containing a single detector probe, at roughly an equimolar concentration relative to that of the RNA amplicon product and suitable to bind to all (n) amplified viral RNAs concurrently. In a preferred implementation, the resulting solution is then applied directly to a single microarray, to allow hybridization at or near room temperature (15° C.-30° C.). The microarray presents at least (n) hybridization probes specific for one or more sequences within each of the (n) TMA-amplified viral RNAs. Analysis of the resulting microarray hybridization pattern is used to detect which among a panel of several viral candidates is present in the sample. Alternatively, within a single virus, probes are chosen which can distinguish wild type sequences from mutant sequences in the virus among at least (n) such sites of the RNA genome. When performed in this manner, the distribution among viruses in a test panel, or the identification of mutations within a virus can be assayed at high throughput in a regional laboratory or at point of collection as in a doctor's office, clinic, or related simple public health venue.

Multiplex Analysis of Bacterial Contamination

A sample containing one or more bacteria is collected from a human or animal subject or from a plant or from a surface, via a swab or from a liquid rinse of the human or animal or surface material under study. The swab or liquid rinse is then dispersed in a saline solution and lysed by heating. RNA is then be extracted by magnetic beads or similar methods. Alternatively, the sample is analyzed directly without RNA extraction.

Concentrated TMA (NASBA) enzyme solution is added to the extracted RNA or lysed solution and then amplified in a two-step isothermal reaction at 65° C. then 41° C. as described above to produce (n) different amplified bacterial RNAs. The product is then used as-is by adding a binding buffer and a plurality of a single or a pair of detector probe nucleotide sequence suitable to bind to all (n) amplified bacterial RNAs, concurrently. In a preferred implementation, the resulting solution is then applied directly to a single microarray, to allow hybridization at or near room temperature (15° C.-30° C.). The microarray presents at least (n) hybridization probes specific for one or more sequences within in each of the (n) TMA (NASBA) amplified bacterial RNAs. Analysis of the resulting microarray hybridization pattern is used to detect which, among a panel of several bacterial candidates, is present in the sample. Alternatively, within a single bacterium, probes are chosen which can distinguish wild type from mutant sequences in the bacterium among at least (n) such sites or to identify markers in a bacterium to identify drug resistance. When performed in this manner, the distribution among bacteria in a test panel, or the identification of mutations within a bacterium or drug resistance markers present in the bacterium can be assayed at high throughput in a regional laboratory or at point of collection as in a doctor's office, clinic, or related simple public health venue.

Multiplex Analysis of Cancer Biomarkers, Mutation, Deletion, Spice Variation on Single Cells A sample containing one or more tumor cells is collected from a human or animal subject, via tissue dissection then dispersion of the tissue, or from a fluid phase tumor cell suspension such as a lymphoid tumor or blood borne metastatic tumor cell. In some instances, the dispersed tumor cells are individually isolated to be used for "Single Cell Analysis". The resulting dispersed tumor cells are then lysed by heating. The RNA from those lysed cells may then be extracted by magnetic beads or similar methods. Alternatively, the sample is analyzed directly without RNA extraction, processing as a very small volume sample (1 µL-10 µL).

Concentrated TMA (NASBA) enzyme solution is then added to the extracted RNA or lysed solution and then amplified as a two-step isothermal reaction once at 65° C. then once at 41° C. to produce (n) different amplified human RNAs bearing meaningful tumor related markers. Such markers may include a panel of local mutational changes to be used for risk prediction or diagnosis or response to treatment. The panel may also include mRNA splice variants useful for tumor analysis or may include RNA transcripts which are greatly over-expressed in the tumor or a tumor related cell type. Subsequent to TMA (NASBA), the product is then used as-is by adding a binding buffer containing a plurality of a single detector probe nucleotide sequence suitable to bind to all (n) amplified tumor cell RNAs, concurrently. The resulting solution is then applied directly to a single Microarray which bears at least (n) hybridization probes specific for one or more sequences in each of the (n) amplified tumor cell RNAs, especially those suitable to detect mutation or deletion or spice variation or the presence of one or more over-expressed mRNA transcripts. Analysis of the resulting Microarray Hybridization pattern is used to detect, among a panel of (n) tumor related genetic changes or splice variations or mRNA species over-expressed in a cell, which of those changes is present in the tumor cell sample under study. When performed in that way, the distribution of mutations or spice variation or greatly altered mRNA transcription can be assayed at high throughput in a regional laboratory or at point of collection as in a doctor's office, clinic, or related simple public health venue.

DetectX-PoCv Assay

The DetectX-PoCv assay is a Point of Care multiplex assay that can test for all variants of Concern and Variants of Interest of a virus in a single reaction at single nucleotide resolution in five (5) simple and easy steps from sample to answer with results in less than 1 hour. A DetectX-PoCv kit, a mini-incubator, and portable handheld sized imager is all that is required to conduct the test. No additional consumables are required.

1. A sample is collected from a dry swab and is fed into an Isothermal reaction tube with an eye dropper. The tube is allowed to incubate for 15 minutes.
2. One drop (1) of Hybridization buffer is then added into the tube, and then closed on the eye-dropper end. The tube is then mixed by swirling.
3. From the eye-dropper end of the tube, four (4) drops of reaction solution are then squeezed into the entry port of a single-glass slide chiplet-microarray. The reaction solution is allowed to hybridize the probes in the chiplet-microarray for 15 minutes.
4. Then four (4) drops of wash solution are then added from the tube, by squeezing the tube into the entry port of the single-glass slide chiplet-microarray. The wash solution is then allowed to sit for 10 minutes, and then drains into the assay fluids collection chamber.
5. The glass slide is inserted into a portable, hand-held imager using the alignment tabs, and Augury software is processed for imaging, results and analysis.

Particularly, DetectX-PoCv assay is a rapid molecular in vitro diagnostic test utilizing an multiplex isothermal nucleic acid amplification technology intended for the qualitative detection of nucleic acid from the SARS-CoV-2 viral RNA and Variants of Concern (VoC)/Variants of Interest (VoI) mutation detection in direct nasal, nasopharyngeal or throat swabs from individuals who are suspected of COVID-19 by their healthcare provider within the first seven days of the onset of symptoms. Results for the identification of SARS-CoV-2 RNA and VoC/VoI mutations are:

1. Covid-19: Measured via Mutation independent Universal Probes
2. Covid-19 Variants of Concern: Alpha—B.1.1.7—U.K, Beta B.1.351—S. Africa, Epsilon—B.1.427—US—California, Epsilon—B.1.429—US—California, Gamma—P.1 Japan/Brazil
3. Covid-19 Variants of Interest: Eta—B.1.525—U.K/Nigeria, Iota—B.1.526—US—New York, B.1.526.1—US—New York, Zeta—P.2—Brazil, B.1.2 SARS-CoV-2

The SARS-CoV-2 RNA and VoC/VoI mutations are generally detectable in respiratory samples during the acute phase of infection. Positive results are indicative of the presence of SARS-CoV-2 RNA and Variants; clinical correlation with patient history and other diagnostic information is necessary to determine patient infection status. Positive results do not rule out bacterial infection or co-infection with other viruses. Testing facilities within the United States and its territories are required to report all results to the appropriate public health authorities. Negative results should be treated as presumptive and, if inconsistent with clinical signs and symptoms or necessary for patient management, should be tested with different authorized or cleared molecular tests. Negative results do not preclude SARS-CoV-2 infection and should not be used as the sole basis for patient management decisions. Negative results should be considered in the context of a patient's recent exposures, history and the presence of clinical signs and symptoms consistent with COVID-19.

Example 2

Multiplex Analysis of Viral Contamination

From December 2019 to May 2021, as the COVID-19 virus spread among multiple nations, it developed multiple stable mutations, especially in its Spike gene, which conferred a selective advantage, enhancing infectivity, thereby enhancing the rate of spread of these variants. In the subsequent 18 months, multiple stable Spike mutations of the virus became evident. It is well known in the art that DNA microarray technology can be used to detect mutations, especially deletions and single nucleotide polymorphism (SNP) of the type seen in the COVID-19 Spike gene. The location of (n) such Spike mutations in the COVID-19 RNA genome is displayed in Table 1. Each of the (n) columns in Table 1 correspond to the location of a specific Spike mutation. To the left of the Table is a list of COVID-19 variants. Inspection of each row of identifies the specific pattern of mutation among the potential set of (n) mutations which can identify each COVID-19 variant. At the bottom of Table 1 is a series of (8) horizontal boxes that identify the position of domains within the Spike gene that can be amplified by RT-PCR. Upon amplification of one or more of those regions to generate a DNA amplimer fragment, the resulting DNA amplimer possesses a DNA sequence capable of binding to a hybridization probe corresponding to each site of potential Spike gene mutation.

TABLE 1

Layout of Hybridization Probes and Primers for Multiplex Analysis of COVID-19 Variants

| | | | CDC % (Mar. 14-27 2021, US) | Incidence % (Gisaid March 2021) | L5F Signal (1-13) | S13I | L18F | T20N | P26S | Q52R | A67V S1 subunit (14-685) N-terminal domain (14-305) | Δ69-70 | D80A/G |
|---|---|---|---|---|---|---|---|---|---|---|---|---|---|
| | Street name | Pango lineage | | | | | | | | | | | |
| VOC | UK | B.1.1.7 | 44.10% | 49.81% | $L^3$ | $S^2$ | $L^3$ | $T^2$ | $P^3$ | $Q^3$ | $A^3$ | $\Delta^1$ | $D^2$ |
| VOC | Cal L452R | B.1.429 | 6.90% | 2.08% | $L^3$ | $I^1$ | $L^3$ | $T^2$ | $P^3$ | $Q^3$ | $A^3$ | $HV^2$ | $D^2$ |
| VOC | Brazil | B.1.427 | 2.90% | 0.90% | $L^3$ | $S/I^1$ | $L^3$ | $T^2$ | $P^3$ | $Q^3$ | $A^3$ | $HV^2$ | $D^2$ |
| VOC | SA | P.1 | 1.40% | 0.39% | $L^3$ | $S^2$ | F | $N^1$ | S | $Q^3$ | $A^3$ | HV | $A^1$ |
| VOC | NYC (Ho et al.) | B.1.351 | 0.70% | 1.13% | F | $S^2$ | $L^3$ | $T^2$ | $P^3$ | $Q^3$ | $A^3$ | HV | $D^2$ |
| VOI | | B.1.526 | 9.20% | 0.82% | L/F | $S^2$ | $L^3$ | $T^2$ | $P^3$ | $Q^3$ | $A^3$ | $HV^2$ | |
| VOI | NYC | B.1.525 | 0.50% | 0.10% | $L^3$ | $S^2$ | $L^3$ | $T^2$ | $P^3$ | R | V | $\Delta^1$ | $D^2$ |
| VOI | Rio de Jan. | P.2 | 0.30% | 0.36% | $L^3$ | $S^2$ | $L^3$ | $T^2$ | $P^3$ | $Q^3$ | $A^3$ | $HV^2$ | $D^2$ |
| | | B.1.2 | 10% | 7.83% | $L^3$ | $S^2$ | $L^3$ | $T^2$ | $P^3$ | $Q^3$ | $A^3$ | $HV^2$ | $D^2$ |
| | | B.1, B.1.1, B.1.234 | 2.4%/ 0.9%/ 0.5% | 2.6%/ 1.5%/ | | | | | | | | | |
| | | B.1.519 | 4.10% | 1.50% | $L^3$ | $S^2$ | $L^3$ | $T^2$ | $P^3$ | $Q^3$ | $A^3$ | $HV^2$ | $D^2$ |
| | | B.1.526.1 | 3.90% | 0.35% | F | $S^2$ | $L^3$ | $T^2$ | $P^3$ | $Q^3$ | $A^3$ | $HV^2$ | G |
| | | B.1.526.2 | 2.90% | 0.18% | F | $S^2$ | $L^3$ | $T^2$ | $P^3$ | $Q^3$ | $A^3$ | $HV^2$ | $D^2$ |
| | | B.1.596 | 1.70% | 1.04% | $L^3$ | $S^2$ | $L^3$ | $T^2$ | $P^3$ | $Q^3$ | $A^3$ | $HV^2$ | $D^2$ |
| | | R.1 | 1.20% | 0.20% | $L^3$ | $S^2$ | $L^3$ | $T^2$ | $P^3$ | $Q^3$ | $A^3$ | $HV^2$ | $D^2$ |
| | | B.1.243, B.1.1.207 | 1.10% | 0.19% | $L^3$ | $S^2$ | $L^3$ | $T^2$ | $P^3$ | $Q^3$ | $A^3$ | $HV^2$ | $D^2$ |
| | | B.1.1.122 | 0.60% | 0.84% | $L^3$ | $S^2$ | $L^3$ | $T^2$ | $P^3$ | $Q^3$ | $A^3$ | $HV^2$ | $D^2$ |
| | US | B.1.375 | <1% | 0.03% | $L^3$ | $S^2$ | $L^3$ | $T^2$ | $P^3$ | $Q^3$ | $A^3$ | $\Delta^1$ | $D^2$ |
| | | B.1.1.1, B.1.416, B.1.1.33, B.1.311, B.1.1.122 | <1% | 0.50% | $L^3$ | $S^2$ | $L^3$ | $T^2$ | $P^3$ | $Q^3$ | $A^3$ | $HV^2$ | D |
| | Brazil (ORIG) | B.1.1.28 | <1% | 0.10% | $L^3$ | $S^2$ | F | $T^2$ | $P^3$ | $Q^3$ | $A^3$ | $HV^2$ | D |
| | Andrah Pradesh | B.1.1.420 | <1% | 0.08% | $L^3$ | $S^2$ | $L^3$ | $T^2$ | $P^3$ | $Q^3$ | $A^3$ | $HV^2$ | D |
| | | A.23.1 | <1% | 0.05% | $L^3$ | $S^2$ | F | $T^2$ | $P^3$ | $Q^3$ | $A^3$ | $HV^2$ | D |
| | | A.27 | <1% | 0.05% | $L^3$ | $S^2$ | F | $T^2$ | $P^3$ | $Q^3$ | $A^3$ | $HV^2$ | D |
| | | A.28 | <1% | 0.02% | $L^3$ | $S^2$ | F | $T^2$ | $P^3$ | $Q^3$ | $A^3$ | $\Delta^1$ | D |
| | Mink/ Cluster V | B.1.1.298 | <1% | 0.00% | $L^3$ | $S^2$ | F | $T^2$ | $P^3$ | $Q^3$ | $A^3$ | $\Delta^1$ | D |
| | | B.1.1.318 | <1% | 0.01% | $L^3$ | $S^2$ | $L^3$ | $T^2$ | $P^3$ | $Q^3$ | $A^3$ | $HV^2$ | D |
| | | B.1.160 | <1% | 1.78% | $L^3$ | $S^2$ | $L^3$ | $T^2$ | $P^3$ | $Q^3$ | $A^3$ | $HV^2$ | D |
| | | B.1.177 | <1% | 3.19% | $L^3$ | $S^2$ | $L^3$ | $T^2$ | $P^3$ | $Q^3$ | $A^3$ | $HV^2$ | D |

TABLE 1-continued

Layout of Hybridization Probes and Primers for Multiplex Analysis of COVID-19 Variants

| | | | | T95I | D138Y | Y144DEL | W152C | F157L/S | L189F | R190S | D215G | A222Y | A243DEL | G252V | D253G |
|---|---|---|---|---|---|---|---|---|---|---|---|---|---|---|---|
| | | | | | | | | F | | | | | | (2B) 150 | |
| | | | | | | | | (1) 101 | | | | | | | |
| | | | | | | | | 3L | | | | | | | |
| | | | | | | | | S1 subunit (14-685) | | | | | | | |
| | | | | | | | | N-terminal domain (14-305) | | | | | | | |
| | Street name | Pango lineage | PCR Amplimer length (bases) | | | | | | | | | | | | |
| | WUHAN | WUHAN | — | | | | | | | | | | | | |
| | B.1.177.80 | | <1% | | | | | | | | | | | | D |
| | B.1.258 | | <1% | | | | | | | | | | HV² | | D |
| | B.1.258.14 | | <1% | | | | | | | | | | HV/Δ¹ | | D |
| | B.1.258.17 | | <1% | | | | | | | | | | Δ¹ | | D |
| | B.1.517 | | 0.04% | | | | | | | | | | HV² | | D |
| | | | 1.15% | | | | | | | | | | | | |
| | | | 0.06% | | | | | | | | | | | | |
| | | | 1.02% | | | | | | | | | | | | |
| | | | 0.25% | | | | | | | | | | | | |
| VOC | UK | B.1.1.7 | | T³ | D² | L³ | W² | F | L³ | P³ | D³ | A³ | A² | G³ | D² |
| VOC | Cal L452R | B.1.429 | | T³ | D² | L³ | C¹ | L³ | L³ | P³ | D³ | A³ | A² | G³ | D² |
| VOC | Brazil | B.1.427 | | T³ | D² | L³ | W/C¹ | F³ | L³ | P³ | D³ | A³ | A² | G³ | D² |
| VOC | SA | P.1 | | T³ | Y1 | L³ | W² | F³ | L³ | P³ | D³ | A³ | A² | G³ | D² |
| VOC | NYC (Ho et al.) | B.1.351 | | I | D² | L³ | W² | F³ | L³ | S | G | A³ | A¹ | G³ | D² |
| VOI | | B.1.526 | | T³ | D² | L³ | W² | F³ | L³ | P³ | D³ | A³ | A² | G³ | G¹ |
| VOI | NYC | B.1.525 | | T³ | D² | Δ¹ | W² | F³ | L³ | P³ | D³ | A³ | A² | G³ | D² |
| VOI | Rio de Jan. | P.2 | | T³ | D² | Y² | W² | F³ | L³ | P³ | D³ | A³ | A² | G³ | D² |
| | | B.1.2 | | T³ | D² | Y² | W² | F³ | L³ | P³ | D³ | A³ | A² | G³ | D² |
| | | B.1, B.1.1, B.1.1.33, B.1.311, B.1.234 | | T³ | D² | Y² | W² | F³ | L³ | P³ | D³ | A³ | A² | G³ | D² |
| | | B.1.1.519 | | T³ | D² | Y² | W² | F³ | L³ | P³ | D³ | A³ | A² | G³ | D² |
| | | B.1.526.1 | | I | D² | Δ¹ | W² | S | L³ | S | D³ | A³ | A² | G³ | D/G¹ |
| | | B.1.526.2 | | T³ | D² | Y² | W² | F³ | L³ | P³ | D³ | A³ | A² | G³ | G¹ |
| | | B.1.596 | | T³ | D² | Y² | W² | F³ | L³ | P³ | D³ | A³ | A² | G³ | D² |
| | | R.1 | | T³ | D² | Y² | L | F³ | L³ | P³ | D³ | A³ | A² | G³ | D² |
| | | B.1.575 | | T³ | D² | Y² | W² | F³ | L³ | P³ | D³ | A³ | A² | G³ | D² |
| | | B.1.243, B.1.1.207 | | T³ | D² | Y² | W² | F³ | L³ | P³ | D³ | A³ | A² | G³ | D² |
| | US | B.1.375 | | T³ | D² | Y² | W² | F³ | L³ | P³ | D³ | A³ | A² | G³ | D² |
| | B.1.1.1, B.1.1416, B.1.1.33, B.1.311, B.1.122 | | | T³ | D² | Y² | W² | F³ | L³ | P³ | D³ | A³ | A² | G³ | D² |
| | Brazil (ORIG) | B.1.1.28 | | T³ | D² | Y² | W² | F³ | L³ | P³ | D³ | A³ | A² | G³ | D² |
| | Andrah Pradesh | B.1.1.420 | | T³ | D² | Y² | W² | F³ | L³ | P³ | D³ | A³ | A² | | D² |
| | | A.23.1 | | T³ | D² | Y² | W² | F³ | L³ | P³ | D³ | A³ | A² | G³ | D² |
| | | A.27 | | T³ | D² | Y² | W² | F³ | L³ | P³ | D³ | V | A² | G³ | D² |
| | | A.28 | | T³ | D² | Y² | W² | F³ | L³ | P³ | D³ | V | | G³ | D² |
| | Mink/ Cluster V | B.1.1.298 | | T³ | D² | Δ¹ | W² | F³ | L³ | R³ | D³ | A³ | A² | G³ | D² |
| | | B.1.1.318 | | T³ | D² | Y² | W² | F³ | L³ | R³ | D³ | A³ | A² | G³ | D² |
| | | B.1.160 | | T³ | D² | ΔY¹ | W² | F³ | L³ | R³ | D³ | A³ | A² | G³ | D² |
| | | B.1.177 | | | | | | | | | | | | | |

TABLE 1-continued

Layout of Hybridization Probes and Primers for Multiplex Analysis of COVID-19 Variants

| | Street name | Pango lineage | CDC % Mar. 14-27 2021 (US) | Incidence % Gisaid March 2021 | V367F | K417N/T | N439K | N440K | L452R | Y453F | S477N | V483A | E484K | S494P | N501Y/T | A570D |
|---|---|---|---|---|---|---|---|---|---|---|---|---|---|---|---|---|
| | | B.1.177.80 | | | V³ | K² | N² | N² | L² | Y² | S² | V | E | S³ | N² | D² |
| | | B.1.258 | | | V³ | K² | N² | N² | L² | Y² | S² | V | E | S³ | N² | D² |
| | | B.1.258.14 | | | V³ | K² | N² | N² | L² | Y² | S² | V | E | S³ | N² | D² |
| | | B.1.258.17 | | | V³ | K² | N² | N² | L² | Y² | S² | V | E | S³ | N² | D² |
| | | B.1.517 | | | V³ | K² | N² | N² | L² | Y² | S² | V | E | S³ | G/V | D² |
| | WUHAN | WUHAN | | | V³ | K² | N² | N² | L² | Y² | S² | V | E | S³ | N² | D² |
| | PCR Amplimer length (bases) | | | | (3) 129 | | | | | | RBD (319-541) | | | | | (4B) 160 |
| | Spike Gene Target Region (Codon) Amino Acid Change | | | | | | | | | | | | | | | |
| VOC | UK | B.1.1.7 | 44.10% | 49.81% | V³/V³ | K²/K² | N²/N² | N²/N² | L²/L² | Y²/Y² | S²/S² | V/V | E/K¹ / E | S/P / S³ | Y¹/N² | D/A³ |
| VOC | Cal L452R | B.1.429 | 6.90% | 2.08% | V³/V³ | K²/K² | N²/N² | N²/N² | L²/R¹ | Y²/Y² | S²/S² | V/V | E/E | S³/S³ | N²/N² | A³/A³ |
| VOC | Brazil | B.1.427 | 2.90% | 0.90% | V³/V³ | K²/K² | N²/N² | N²/N² | R¹/L² | Y²/Y² | S²/S² | V/V | E/E | S³/S³ | N²/N² | A³/A³ |
| VOC | | P.1 | 1.40% | 0.39% | V³/V³ | N/T¹ / K² | N²/N² | N²/N² | L²/L² | Y²/Y² | S²/S² | V/V | K¹/K¹ | S³/S³ | Y¹/Y¹ | A³/A³ |
| VOC | SA | B.1.351 | 0.70% | 1.13% | V³/V³ | K²/K² | N²/N² | N²/N² | L²/L² | Y²/Y² | S²/S² | V/V | K¹/E/K¹ | S³/S³ | Y¹/N² | A³/A³ |
| VOI | NYC (Ho et al.) | B.1.526 | 9.20% | 0.82% | V³/V³ | K²/K² | N²/N² | N²/N² | L²/L² | Y²/Y² | S²/S/N¹ | V/V² | E/K¹ | S³/S³ | N²/N² | A³/A³ |
| VOI | NYC | B.1.525 | 0.50% | 0.10% | V³/V³ | K²/K² | N²/N² | N²/N² | L²/L² | Y²/Y² | S²/S² | V/V | K¹/K¹ | S³/S³ | N²/Y¹ | A³/A³ |
| VOI | Rio de Jan. | P.2 | 0.30% | 0.36% | V³/V³ | K²/K² | N²/N² | N²/N² | L²/L² | Y²/Y² | S²/S² | V/V | E/E | S³/S³ | N²/N² | A³/A³ |
| | | B.1.2 | 10% | 7.83% | V³/V³ | K²/K² | N²/N² | N²/N² | L²/L² | Y²/Y² | S²/S² | V/V | E/E | S³/S³ | N²/N² | A³/A³ |
| | | B.1, B.1.1, B.1.234 | 2.4%/0.9%/0.5% | 2.6%/1.5% | V³ | K² | N² | N² | L² | Y² | S² | V | E | S³ | N² | A³ |
| | | B.1.1.519 | 4.10% | 1.50% | V³/V³ | K²/K² | N²/N² | N²/N² | L²/R¹ | Y²/Y² | S²/S² | V/V | E/E | S³/S³ | N²/N² | A³/A³ |
| | | B.1.526.1 | 3.90% | 0.35% | V³/V³ | K²/K² | N²/N² | N²/N² | L²/L² | Y²/Y² | S²/S² | V/V² | E/E | S³/S³ | N²/N² | A³/A³ |
| | | B.1.526.2 | 2.90% | 0.18% | V³/V³ | K²/K² | N²/N² | N²/N² | L²/L² | Y²/Y² | S²/S² | V/V | K¹/E | S³/S³ | N²/N² | A³/A³ |
| | | B.1.596 | 1.70% | 1.04% | V³/V³ | K²/K² | N²/N² | N²/N² | L²/L² | Y²/Y² | S²/S² | V/V | E/E | S³/S³ | N²/N² | A³/A³ |
| | | R.1 | 1.20% | 0.20% | V³/V³ | K²/K² | N²/N² | N²/N² | L²/L² | Y²/Y² | S²/S² | V/V | K¹/E | S³/S³ | N²/N² | A³/A³ |
| | | B.1.575 | 1.10% | 0.19% | V³/V³ | K²/K² | N²/N² | N²/N² | L²/L² | Y²/Y² | S²/S² | V/V | E/E² | S³/S³ | N²/N² | A³/A³ |
| | | B.1.243, B.1.1.207 | 0.60% | 0.84% | V³/V³ | K²/K² | N²/N² | N²/N² | L²/L² | Y²/Y² | S²/S² | V/V² | E²/E² | S³/S³ | N²/N² | A³/A³ |
| | US B.1.1.1, B.1.416, B.1.1.33, B.1.311, B.1.122 | B.1.375 | <1% | 0.03%/0.50% | V³ | K² | N² | N² | L² | Y² | S² | V² | E² | S³ | N² | A³ |
| | Brazil (ORIG) | B.1.1.28 | <1% | 0.10% | V³ | K² | N² | N² | L² | Y² | S² | V² | E² | S³ | N² | A³ |
| | Andrah Pradesh | B.1.1.420 | <1% | 0.08% | V³ | K² | N² | K¹ | L² | Y² | S² | V² | E² | S³ | N² | A³ |
| | | A.23.1 | <1% | 0.05% | F/V³ | K²/K² | N²/N² | N²/N² | L²/R¹ | Y²/Y² | S²/S² | V²/V² | E/K¹/E² | S³/S³ | N²/Y¹ | A³/A³ |
| | | A.27 | <1% | 0.05% | | | | | | | | | | | | |

TABLE 1-continued

Layout of Hybridization Probes and Primers for Multiplex Analysis of COVID-19 Variants

|  |  | Pango lineage | Q613H | D614G | H655Y | Q677P/H | P681H | I692V | A701V | T716I | G769V | D796Y | F856L | S982A | T1027I | D1118H | V1176F |
|---|---|---|---|---|---|---|---|---|---|---|---|---|---|---|---|---|---|
|  | Mink/Cluster V | A.28 | <1% | 0.02% | V³ | K² | N² | I² | L² | Y² | S² | V² | E² | S³ | T³ | T | A³ |
|  |  | B.1.1.298 | <1% | 0.00% | V³ | K² | N² | I² | L² | Y² | N¹ | V² | K¹ | S³ | T³ | N² | A³ |
|  |  | B.1.1.318 | <1% | 0.01% | V³ | K² | N² | I² | L² | Y² | S² | V² | E² | S³ | T³ | N² | A³ |
|  |  | B.1.429 | <1% | 1.78% | V³ | K² | N² | I² | L² | Y² | S² | V² | E² | S³ | T³ | N² | A³ |
|  |  | B.1.160 | <1% | 3.19% | V³ | K² | N² | I² | L² | Y² | S² | V² | E² | S³ | T³ | N² | A³ |
|  |  | B.1.177 | <1% | 0.04% | V³ | K² | N² | I² | L² | Y² | S² | V² | E² | S³ | T³ | N² | A³ |
|  |  | B.1.177.80 | <1% | 1.15% | V³ | K² | N² | I² | L² | Y² | S² | V² | E² | S³ | T³ | N² | A³ |
|  |  | B.1.258 | <1% | 0.06% | V³ | K² | N² | I² | L² | Y² | S² | V² | E² | S³ | T³ | N² | A³ |
|  |  | B.1.258.14 | <1% | 1.02% | V³ | K² | N² | I² | L² | Y² | S² | V² | E² | S³ | T³ | N² | A³ |
|  |  | B.1.258.17 | <1% | 0.25% | V³ | K² | N² | I² | L² | Y² | S² | V² | E² | S³ | T³ | T | A³ |
|  |  | B.1.517 | — | — | V³ | K² | N² | I² | L² | Y² | S² | V² | E² | S³ | T³ | N² | A³ |
|  | WUHAN | WUHAN | | | | | | | | | | | | | | | |
| PCR Amplimer length (bases) | | | | | | | (5) 199 | | | | (6) 151 | | | | | | |
|  |  | Street name | | | | | P681H | I692V | A701V | T716I | G769V | D796Y | F856L | S982A | T1027I | D1118H | V1176F |
|  |  | | | | | | | | | | | S2 subunit (AA 686-1273) | | | | | |
|  |  | | | | | | | | | | | Fusion Peptide (786-806) | | | | | |
| VOC | UK | B.1.1.7 | Q² | G¹ | H³ | Q² | H¹ | I² | A² | T³ | G³ | D³ | F³ | S³ | T³ | D³ | V³ |
| VOC | Cal L452R | B.1.429 | Q² | G¹ | H³ | Q² | P² | I² | A² | T³ | G³ | D³ | F³ | S³ | T³ | D³ | V³ |
| VOC | Brazil | B.1.427 | Q² | G¹ | H³ | Q² | P² | I² | A² | T³ | G³ | D³ | F³ | S³ | T³ | D³ | V³ |
| VOC | SA | P.1 | Q² | G¹ | Y | Q² | P² | I² | A/V¹ | T³ | G³ | D³ | F³ | S³ | T³ | D³ | F |
| VOI | NYC (Ho et al.) | B.1.351 | Q² | G¹ | H³ | Q² | P² | I² | A² | T³ | G³ | D³ | F³ | S³ | T³ | D³ | V³ |
|  |  | B.1.526 | Q² | G¹ | H³ | Q² | P² | I² | V | T³ | G³ | D³ | F³ | S³ | T³ | D³ | V³ |
| VOI | NYC | B.1.525 | Q² | G¹ | H³ | Q² | P² | I² | A² | T³ | G³ | D³ | F³ | S³ | T³ | D³ | V³ |
| VOI | Rio de Jan. | P.2 | Q² | G¹ | H³ | H | P² | I² | A² | T³ | G³ | D³ | F³ | S³ | T³ | D³ | F |
|  |  | B.1.2 | Q² | G¹ | H³ | Q² | P² | I² | A² | T³ | G³ | D³ | F³ | S³ | T³ | D³ | V³ |
|  |  | B.1, B.1.1, B.1.234 | Q² | G¹ | H³ | Q² | P² | I² | A/V¹ | T³ | G³ | D³ | F³ | S³ | T³ | D³ | V³ |
|  |  | B.1.1.519 | Q² | G¹ | H³ | Q² | P² | I² | A² | T³ | G³ | D³ | F³ | S³ | T³ | D³ | V³ |
|  |  | B.1.526.1 | Q² | G¹ | H³ | Q² | P² | I² | A/V¹ | T³ | G³ | D³ | F³ | S³ | T³ | D³ | V³ |
|  |  | B.1.526.2 | Q² | G¹ | H³ | Q² | P² | I² | A² | T³ | G³ | D³ | F³ | S³ | T³ | D³ | V³ |
|  |  | B.1.596 | Q² | G¹ | H³ | Q² | P² | I² | A² | T³ | G³ | D³ | F³ | S³ | T³ | D³ | V³ |
|  |  | R.1 | Q² | G¹ | H³ | QP¹ | P² | I² | A² | T³ | V | D³ | F³ | S³ | T³ | D³ | V³ |
|  |  | B.1.575 | Q² | G¹ | H³ | Q² | P² | I² | A² | T³ | G³ | D³ | F³ | S³ | T³ | D³ | V³ |
|  |  | B.1.243, B.1.1.207 | Q² | G¹ | H³ | Q² | H¹ | I² | A² | I | G³ | D³ | F³ | S³ | T³ | D³ | V³ |
|  | US | B.1.375 | Q² | D² | H³ | Q² | H¹ | I² | A² | T³ | G³ | D³ | F³ | S³ | T³ | D³ | V³ |
|  |  | B.1.1.1, B.1.1.33, B.1.1.311, B.1.1.122 | Q² | D² | H³ | Q² | P² | I² | A² | T³ | G³ | D³ | F³ | S³ | T³ | D³ | V³ |
|  | Brazil (ORIG) | B.1.1.28 | Q² | G¹ | H³ | Q² | P² | I² | A² | T³ | G³ | D³ | F³ | S³ | T³ | D³ | F |
|  | Andrah Pradesh | B.1.1.420 | Q² | G¹ | Y | Q² | P² | I² | A² | T³ | G³ | D³ | F³ | S³ | T³ | D³ | V³ |
|  |  | A.23.1 | Q² | G¹ | H³ | Q² | P² | I² | A² | T³ | G³ | D³ | F³ | S³ | T³ | D³ | V³ |
|  |  | A.27 | Q² | G¹ | H³ | Q² | P² | I² | A² | T³ | G³ | D³ | F³ | S³ | T³ | D³ | V³ |

TABLE 1-continued

Layout of Hybridization Probes and Primers for Multiplex Analysis of COVID-19 Variants

| | | | | | | | | | | | | | | | |
|---|---|---|---|---|---|---|---|---|---|---|---|---|---|---|---|
| Mink/Cluster V | A.28 | $Q^2$ | $G^1$ | $H^3$ | $Q^2$ | $P^2$ | $I^2$ | $A^2$ | $T^3$ | $G^3$ | $D^3$ | $F^3$ | $S^3$ | $T^3$ | $D^3$ | $V^3$ |
| | B.1.1.298 | $Q^2$ | $G^1$ | $H^3$ | $Q^2$ | $P^2$ | $I^2$ | $A^2$ | $T^3$ | $G^3$ | $D^3$ | $F^3$ | $S^3$ | $T^3$ | $D^3$ | $V^3$ |
| | B.1.1.318 | $Q^2$ | $G^1$ | $H^3$ | $Q^2$ | $P^2$ | $I^2$ | $A^2$ | $T^3$ | $G^3$ | $D^3$ | $F^3$ | $S^3$ | $T^3$ | $D^3$ | $V^3$ |
| | B.1.160 | $Q^2$ | $G^1$ | $H^3$ | $Q^2$ | $P^2$ | $I^2$ | $A^2$ | $T^3$ | $G^3$ | $D^3$ | $F^3$ | $S^3$ | $T^3$ | $D^3$ | $V^3$ |
| | B.1.177 | $Q^2$ | $G^1$ | $H^3$ | $Q^2$ | $P^2$ | $I^2$ | $A^2$ | $T^3$ | $G^3$ | $D^3$ | $F^3$ | $S^3$ | $T^3$ | $D^3$ | $V^3$ |
| | B.1.177.80 | $Q^2$ | $G^1$ | $H^3$ | $Q^2$ | $P^2$ | $I^2$ | $A^2$ | $T^3$ | $G^3$ | $D^3$ | $F^3$ | $S^3$ | $T^3$ | $D^3$ | $V^3$ |
| | B.1.258 | $Q^2$ | $G^1$ | $H^3$ | $Q^2$ | $P^2$ | $I^2$ | $A^2$ | $T^3$ | $G^3$ | $D^3$ | $F^3$ | $S^3$ | $T^3$ | $D^3$ | $V^3$ |
| | B.1.258.14 | $Q^2$ | $G^1$ | $H^3$ | $Q^2$ | $P^2$ | $I^2$ | $A^2$ | $T^3$ | $G^3$ | $D^3$ | $F^3$ | $S^3$ | $T^3$ | $D^3$ | $V^3$ |
| | B.1.258.17 | $Q^2$ | $G^1$ | $H^3$ | $Q^2$ | $P^2$ | $I^2$ | $A^2$ | $T^3$ | $G^3$ | $D^3$ | $F^3$ | $S^3$ | $T^3$ | $D^3$ | $V^3$ |
| | B.1.517 | $Q^2$ | $G^1$ | $H^3$ | $Q^2$ | $P^2$ | $I^2$ | $A^2$ | $T^3$ | $G^3$ | $D^3$ | $F^3$ | $S^3$ | $T^3$ | $D^3$ | $V^3$ |
| WUHAN | WUHAN | $Q^2$ | $D^2$ | $H^3$ | $Q^2$ | $P^2$ | $I^2$ | $A^2$ | $T^3$ | $G^3$ | $D^3$ | $F^3$ | $S^3$ | $T^3$ | $D^3$ | $V^3$ |
| PCR Amplimer length (bases) | | | (7) 88 | | | (8) 135 | | | | | | | | | | |

[1] AA mutation-hybridizes to mutation specific probe
[2] AA identical to hCoV-19/Wuhan/WIV04/2019 (WIV04)-official reference sequence employed by GISAID (EPI_ISL_402124) Hybridizes to reference specific probe
[3] Potential probe target The detector probe and correspondingly, the detector probe binding nucleotide sequence, may be altered to include a large number of alternative sequences, thus enabling the binding of a variety of detector probes, keeping in mind a Detector Probe length in the range of 15 to 30 bases with a GC content from about 40% to about 60%.

TABLE 2

Primer Sequences used for TMA Reactions

| SEQ ID NO | Amplimer # | Target | Gene | Primer Sequence (5' to 3') |
|---|---|---|---|---|
| 1 | 1 | AA11-33 | Spike | TCTAATACCTTTGCTCATTGAC-(TTTTTTTCTTGTTTTATTGCCACTAGTC) |
| 2 | | AA11-33 | Spike | TACAAT-TAATACGACTCACTATAGG-GCATA-(TTTTTGTCAGGGTAATAAACACCACGTG) |
| 3 | 2 | AA64-80 | Spike | TCTAATACCTTTGCTCATTGAC-(ACCTTTCTTTTCCAATGTTACTTGGTTC) |
| 4 | | AA64-80 | Spike | TACAAT-TAATACGACTCACTATAGG-GCATA-(TTTTATGTTAGACTTCTCAGTGGAAGCA) |
| 5 | 3 | AA126-157 | Spike | TCTAATACCTTTGCTCATTGAC-(TTTCTTATTGTTAATAACGCTACTAATG) |
| 6 | | AA126-157 | Spike | TACAAT-TAATACGACTCACTATAGG-GCATA-(TTTCATTCGCACTAGAATAAACTCTGAA) |
| 7 | 4 | AA213-260 | Spike | TCTAATACCTTTGCTCATTGAC-(TTTTAAGCACACGCCTATTAATTTAGTG) |
| 8 | | AA213-260 | Spike | TACAAT-TAATACGACTCACTATAGG-GCATA-(TTTCCACATAATAAGCTGCAGCACCAGC) |
| 9 | 5 | AA408-456 | Spike | TCTAATACCTTTGCTCATTGAC-(TGTAATTAGAGGTGATGAAGTCAGA) |
| 10 | | AA408-456 | Spike | TACAAT-TAATACGACTCACTATAGG-GCATA-(TTTAAAGGTTTGAGATTAGACTTCCTAA) |
| 11 | 6 | AA475-505 | Spike | TCTAATACCTTTGCTCATTGAC-(TTTTATTTCAACTGAAATYTATCAGGCC) |
| 12 | | AA475-505 | Spike | TACAAT-TAATACGACTCACTATAGG-GCATA-(TTTAAAGTACTACTACTCTGTATGGTTG) |
| 13 | 7 | AA603-618 | Spike | TCTAATACCTTTGCTCATTGAC-(TTTAGTGTTATAACACCAGGAACAAATA) |
| 14 | | AA603-618 | Spike | TACAAT-TAATACGACTCACTATAGG-GCATA-(TTTTGCATGAATAGCAACAGGGACTTCT) |
| 15 | 8 | AA677-707 | Spike | TCTAATACCTTTGCTCATTGAC-(TTTTGCAGGTATATGCGCTAGTTATCAG) |
| 16 | | AA677-707 | Spike | TACAAT-TAATACGACTCACTATAGG-GCATA-(TTTTGGTATGGCAATAGAGTTATTAGAG) |

Microarray Hybridization Probe Sequences

Hybridization probe sequences designed for hybridization to (n) multiplex RT-PCR amplimers, remain suitable without modification for hybridization to the corresponding set of (8) multiplex TMA (NASBA) (RT-T7) amplimers. Table 3 describes wild-type, mutant and universal probes (U) suitable for detecting both wild type and mutant sequences ("U" in Target identifier column, Table 3).

TABLE 3

Hybridization Probe Sequences used for Microarray Analysis

| SEQ ID NO | Amplimer # | Target | Probe Sequence (5' to 3') |
|---|---|---|---|
| 17 | 1 | 13U-SE-RE1.2 | TTTTTCTAGTCTCTAKTCAGTGTGTTTTTT |
| 18 | 1 | 13S-SE-RE1.2 | TTTTTTTGTCTCTAGTCAGTGTTTTTTTTT |
| 19 | 1 | 13I-SE-RE1.1 | TTTTTTTAGTCTCTATTCAGTGTTTTTTTT |
| 20 | 1 | 20U-SE-RE1.1 | TTTTTTAATYTTACAAMCAGAACTCTTTTT |
| 21 | 1 | 20T-SE-RE1.1 | TTTTTTTATCTTACAACCAGAACCTTTTTT |
| 22 | 1 | 20T-SE-RE1.2 | TTTTTTTATCTTACAACCAGAACTTTTTTT |
| 23 | 2 | AA69-70 HV | TTTTTCCCATGCTATACATGTCTCTGTTTTTT |
| 24 | 2 | AA69-70 DEL | TTTTTTTTTCCATGCTATCTCTGGGATTTTTT |
| 25 | 2 | AA_D80A | TTTTTCAGAGGTTTGMTAACCCTGTCTTTTTT |
| 26 | 2 | AA_D80_ | TTTTTTTGGTTTGATAACCCTGCTTTTTTT |
| 27 | 2 | AA_80A | TTTTTTTGGTTTGCTAACCCTGCTTTTTTT |
| 28 | 3 | AA_D138Y | TTTTATTTTGTAATKATCCATTTTGTTTT |
| 29 | 3 | AA_D138_ | TTTTTCTTTGTAATGATCCATTTTCTTTTT |
| 30 | 3 | AA_138Y | TTTTTTTTGTAATTATCCATTTTCTTTTT |
| 31 | 3 | AA_W152C | TTTTTAGTTGKATGGAAAGTGAGTTCTTTT |
| 32 | 3 | AA_W152_ | TTTCTCTAAAAGTTGGATGGAAACTCTTCT |
| 33 | 3 | AA_152C | TTTCTTCAAAGTTGTATGGAAAGCCTTCTT |
| 34 | 4 | AA_A243_ | TTTTTTTTCAAACTTTACTTGCTTTACTCTTT |
| 35 | 4 | AA_243DEL | TTTTTTTTCAAACTTTACATAGAAGCCTTTTT |
| 36 | 4 | AA_R246_ | TTTTCTACATAGAAGTTATTTGACTCCCTTTT |
| 37 | 4 | AA_246I | TTTTCTGCTTTACATATGACTCCTGGTTTTTT |
| 38 | 4 | AA_D253G | TTTCTACTCCTGGTGRTTCTTCTTCATTTT |
| 39 | 4 | AA_D253_ | TTTTTTCCCTGGTGATTCTTCTTTCTTTTT |
| 40 | 4 | AA_253G | TTTTTTCCCTGGTGGTTCTTCTTTTTTTTT |
| 41 | 5 | AA_439K+N440K | TTTTTAATTCTAAMAAKCTTGATTCTAATTTT |
| 42 | 5 | AA_N439_+N440_ | TTTTTAATTCTAACAATCTTGATTTCTTTT |
| 43 | 5 | AA_N439_+_440K | TTTTTATTCTAACAAGCTTGATTTTTTTT |
| 44 | 5 | AA_439K+N440_ | TTTTcTATTCTAAAAATCTTGATTTCTTTT |
| 45 | 5 | AA_L452R | TTTCTATAATTACCTGTATAGATTGTCTTT |
| 46 | 5 | AA_L452_ | TTTTTTTAATTACCTGTATAGATTTCTTTT |

TABLE 3-continued

Hybridization Probe Sequences used for Microarray Analysis

| SEQ ID NO | Amplimer # | Target | Probe Sequence (5' to 3') |
|---|---|---|---|
| 47 | 5 | AA_452R | TTTTTCATAATTACTGGTATAGATCTTTTT |
| 48 | 6 | AA_S477_ | TTTTTTCGCCGGTAGCACACCTCTTTTTTT |
| 49 | 6 | AA_477N | TTTTCTTCCGGTAACACACCTTTTTTTTT |
| 50 | 6 | AA_V483A+E484K | TTTTTTAATGGTGTTRAAGGTTTTAATTTTTT |
| 51 | 6 | AA_V483_+E484_ | TTTTTTCTGGTGTTGAAGGTTTTACTTTTT |
| 52 | 6 | AA_V483_+_484K | TTTTTTTATGGTGTTAAAGGTTTTCTTTTT |
| 53 | 6 | AA_483A+E484_ | TTTTTTTATGGTGCTGAAGGTTCTTTTTTT |
| 54 | 6 | AA_N501Y | TTTTTTTTCCAACCCACTWATGGTGTTTTTTTT |
| 55 | 6 | AA_N501_ | TTTTTTTTACCCACTAATGGTGTCTTTTTT |
| 56 | 6 | AA_N_501Y | TTTTTTTTACCCACTTATGGTGTCTTTTTT |
| 57 | 8 | AA_Q677P/H | TTTTTTATCAGACTCMGACTAATTCTCTTTTT |
| 58 | 8 | AA_Q677_ | TTTTTTCCAGACTCAGACTAATTTCTTTTT |
| 59 | 8 | AA_677P | TTTTTCTTCAGACTCCGACTAATCTTTTTT |
| 60 | 8 | AA_677H1 | TTTTTTCCAGACTCATACTAATTTCTTTTT |
| 61 | 8 | AA_677H2 | TTTTTTCCAGACTCAGACTAATTTCTTTTT |
| 62 | 8 | AA_P681H | TTTTTTCAGACTAATTCTCMTCGGCTTTTT |
| 63 | 8 | AA_P681_ | TTTTTTTCTAATTCTCCTCGGCGTTTTTTT |
| 64 | 8 | AA_681H | TTTTTTTTTAATTCTCATCGGCGTTTTTTT |
| 65 | 8 | AA_A701V | TTTTCACTTGGTGYAGAAAATTCAGTTTTT |
| 66 | 8 | AA_A701_ | TCTTCTTCTTGGTGCAGAAAATTATTCTTT |
| 67 | 8 | AA_701V | TCTTCTTCTTGGTGTAGAAAATTATTCTTT |

The assay was verified via NIH-RADx Blinded Variant panel (comprising the clinical samples) from Emory RADx Clinical Core site. These clinical samples were confirmed as bonafide variants via Next Generation Sequencing. The blinded panel comprised 10 different variants, 52 samples in serial dilutions resulting in 100% detection of all Variants on the DetectX-Cv assay and signed off by the RADx Variant task Force. The assay performance showed a similar "Limit of Analysis" (LOA) for all variants tested, which in terms of the qPCR analysis performed by RADx on each sample, comprised a LoA of @28-30, to be compared to a Limit of Detection (LOD) for the same test of 32-35. The Residual unprocessed samples from the NIH-RADx Blinded Variant panel were sent to TriCore Reference Labs, New Mexico. TriCore analysis had also identified 100% of the Variants. The Limit of Analysis obtained in these TriCore data was identical or, in two instances one dilution lower (higher Ct) than that obtained previously. TriCore Reference Labs also processed 28 clinical samples. FIGS. 3A-3D show a subset of the results. Individual plots are available upon request for the full complement of clinical samples. FIGS. 4-7 illustrate the abilities of the arrays to correctly identify variants.

Example 3

Multiplex NASBA Microarray Detection of a Mixture of SARS-CoV-2, Influenza A and Influenza B Multiplex NASBA Microarray Assay Genomic RNA reference reagents and oligonucleotides (NASBA primers, Detector Probes and Hybridization Probes) that are used are listed in Table 4 and Table 5.

TABLE 4

Genomic RNA Reference Reagents

| Reagent | Source | Identifier |
|---|---|---|
| SARS-CoV-2 virus Genomic RNA | ATCC | NR-52507 |
| Influenza A virus (H1N1) Genomic RNA | ATCC | VR-95DQ |
| Influenza B virus (Yamagata) Genomic RNA | ATCC | VR-1804DQ |

TABLE 4-continued

Genomic RNA Reference Reagents

| Reagent | Source | Identifier |
|---|---|---|
| Universal Human Reference RNA | ThermoFisher Scientific | QS0639 |
| NASBA liquid kit | Life Sciences Advanced Technologies Inc. | SKU: NWK-1 |
| Nuclease-Free Water | ThermoFisher Scientific | AM9938 |
| Streptavidin, R-phycoerythrin conjugate (SAPE) | ThermoFisher Scientific | S866 |

TABLE 5

Sequence of NASBA primers, Detector Probes and Hybridization Probes

| SEQ ID NO | Primers and Probes | Nucleotide Sequences |
|---|---|---|
| | SARS-CoV-2 NASBA Primers | |
| 72 | 447-FP-99296-Flag1-23 | TTTTAATCGGTGCTCTTGACCAAATTGCAATCTTGATTCTAAGGTTGGTG |
| 73 | 501.RP-99243-T7-2 | GAATTTAATACGACTCACTATAGGGATAATAAAGTACTACTACTCTGTATGGTTG |
| | SARS-CoV-2 Hybridization Probes | |
| 74 | 452U-SE-RE1.1 | TTTCTATAATTACCDGTATAGATTGCTTT |
| 75 | 452L-SE-RE1.2 | TTTTTTTAATTACCTGTATAGATTTCTTTT |
| 76 | 452R-SE-RE1.5 | TTTTTCATAATTACCGGTATAGATCTTTTT |
| 77 | 452Q-SE-RE1.2 | TTTTTTTTAATTACCAGTATAGACTTTTTT |
| 78 | S477N-SE-RE1.2 | TTTTTCGCCGGTARCAMACCTTGTATTTTT |
| 79 | T478K-SE-RE1.1 | TTTTTCGGTAGCAMACCTTGTAATGTTTTT |
| 80 | T478-SE-RE1.2 | TTTTTTTGGTAGCACACCTTGTTTTTTTTT |
| 81 | 478K-SE-RE1.5 | TTTTTTTGTAGCAAACCTTGTATTTTTTTT |
| 82 | 484U-SE-RE1.1 | TAATGGTGYTRMAGGTTTTAATTTTTT |
| 83 | 483V484E-SE-RE1.7 | TTTTTTCTGGTGTTGAAGGTTTTACTTTTT |
| 84 | 484K-SE-RE1.5 | TTTTTTTATGGTGTTAAAGGTTTTCTTTTT |
| 85 | 483A-SE-RE1.3 | TTTTTTTATGGTGCTGAAGGTTCTTTTTTT |
| 86 | V483_._484A-RE1.2 | TTTTTTCGGTGTTGCAGGTTTTATCTTTTT |
| 87 | F490S-SE-RE1.1 | TTTTCTAATTGTTACTYTCCTTTACAATTTTT |
| 88 | F490-SE-RE1.1 | TTTTTTTTTGTTACTTTCCTTTACTTTTTT |
| 89 | 490S-SE-RE1.1 | TTTTTTTTTGTTACTCTCCTTTACTTTTTT |
| 90 | 493.494-SE-RE1.3 | TCCTTTACAAYCATATGGTTTTTTTT |
| 91 | | TTACGATCATATAGTTTCCTTTTT |
| 92 | S494-SE-RE1.1 | CTTTACAATCATATGGTCTTTTT |
| 93 | 494P-SE-RE1.1 | TTTTTCTCTTTACAACCATATGGTCTTTTT |
| 94 | _493R._496S-RE1.1 | TTTTTCTTACGATCATATAGTTTCTTTTTT |
| 95 | 501UNI-SE-RE1.1 | TTTTTTTTCCAACCCACTWATGGTGTTTTTTT |

TABLE 5-continued

Sequence of NASBA primers, Detector Probes and Hybridization Probes

| SEQ ID NO | Primers and Probes | Nucleotide Sequences |
|---|---|---|
| 96 | 501N-SE-RE1.4 | TTTTTTTTACCCACTAATGGTGTCTTTTTT |
| 97 | 501Y-SE-RE1.4 | TTTTTTTTACCCACTTATGGTGTCTTTTTT |
|  | SARS-CoV-2 Detector Probes |  |
| 98 | 99089-Biotin(Biotin-Flag1) | /5Biosg/TTTTAATCGGTGCTCTTGACCAAATTG |
| 99 | Biotinylated-Amp6-tag (501.RP-99243-T7-2) | /5Biosg/TTTTTTGAGAGAGATATTTCAACTGATTT |
| 100 | Cy3-Flag3-tag (Paer3-RP-1.4-C3) | /5Cy3/TTTCTACCGTACTCTAGCTTT |
| 101 | Cy3-TMA5-tag (TMA5-15MER-C3) | /5Cy3/TTTCTGTTGAGTTATCCCTTT |
|  | Influenza A NASBA Primers |  |
| 102 | infA-FP-Lau-Flag3-23 | TTTCTACCGTACTCTAGCTACTTCTAACCGAGGTCGAAACGTA |
| 103 | infA-RP-99083-T7-TMA5-23 | GAATTAATACGACTCACTATAGGGATAACTCAACAGGCATTYTGGACAAAKCGTCTACG |
|  | Influenza A Hybridization Probe |  |
| 104 | lnfA.7.univ-pubRev | TTTTTCGTGCCCAGTGAGCGAGGACTGCATTTTT |
|  | Influenza B NASBA Primers |  |
| 105 | infB-FP-99086-Flag3-23 | TTTCTACCGTACTCTAGCTATCCTCAACTCACTCTTCGAGCG |
| 106 | infB-RP-99089-T7-TMA5-23 | GAATTAATACGACTCACTATAGGGATAACTCAACAGATCGGTGCTCTTGACCAAATTGG |
|  | Influenza B Hybridization Probe |  |
| 107 | lnfB.8.univ-pub | TTTTCCAATTCGAGCAGCTGAAACTGCGGTGTTTTT |
|  | Influenza A and B Detector Probes |  |
| 108 | Flag3-Biot | /5Biosg/TTTCTACCGTACTCTAGCTTT |
| 109 | TMA5-15MER-BIOT | /5Biosg/TTTCTGTTGAGTTATCCCTTT |
|  | B2M NASBA Primers |  |
| 110 | B2M-FP-99320-Flag3 | TTTCTACCGTACTCTAGCTGCCTGCCGTGTGAACCATGTGA |
| 111 | B2M-RP-99150-T7-TMA5 | AATTTAATACGACTCACTATAGGGATAACTCAACAGTGGAATTCATCCAATCCAAATGCG |

TABLE 5-continued

Sequence of NASBA primers, Detector Probes and Hybridization Probes

| SEQ ID NO | Primers and Probes | Nucleotide Sequences |
|---|---|---|
| | B2M Hybridization Probe | |
| 112 | B2M_RE2.1 | TTTTTAGCATCATGGAGGTTTGAAGTTTTT |
| | B2M NASBA Detector Probe | |
| 108 | Flag3-Biot | /5Biosg/TTTcTACCGTACTCTAGCTTT |
| 109 | TMA5-15MER-BIOT | /5Biosg/TTTCTGTTGAGTTATCCCTTT |

During the multiplex TMA (NASBA) reaction, primer mediated isothermal amplification produces RN amplicons which acquire detector probe binding sequences which are suitable to bind fluorescently labeled detector probes that are introduced in the hybridization or wash buffers, thereby forming a [Hybridization Probe-RNA amplicon-Detector Probe] "Sandwich". The Detector Probes are DNA oligonucleotides synthesized with a biotin group at their 5' termini (Table 5). When mixed with Streptavidin modified Phycoerythrin (SAFE), a SAFE-detector probe complex is formed, thereby labeling the RNA amplicon as bound to its cognate hybridization probe.

Method

Step 1: NASBA Reaction

Primer mix and reaction components are listed in Table 6 and Table 7. The reaction is carried out according to the manufacturer's manual (Life Sciences Advanced Technologies) with modifications. Human beta-2-microglobulin RNA is used as a control. Briefly, the method is as follows:

1. Denaturation of RNA template and anneal primers to the template. For each reaction,
   1) Mix 6.7 ul of 3×NASBA reaction buffer (NECB-1-24) and 3.3 ul of 6× Nucleotide Mix (NECN-1-24) and warm the mixture at 41° C. for 5 minutes.
   2) To the mixture, add 1 ul of RNA template, and 3.38 ul primer mix (see Table 6 for primer mix composition).
   3) Mix gently and incubate the mixture at 95° C. for 5 minutes, followed by a 10-min incubation at 41° C.
2. Amplification of targets.
   1) Warm the enzyme mixture (NEC-1-24) to 41° C.
   2) Add 5 ul of the enzyme mixture to the reaction and incubate at 41° C. for 1 hour, followed by a 10-min at 65° C. before hybridization.

TABLE 6

Primer mix for one reaction

| Primer | Volume | Stock concentration | Final concentration in the reaction |
|---|---|---|---|
| B2M-FP-99320-Flag3 | 0.25 ul | 2 uM | 25 nM |
| B2M-RP-99150-T7-TMA5 | 0.25 ul | 2 uM | 25 nM |
| infA-FP-Lau-Flag3-23 | 0.75 ul | 2 uM | 75 nM |
| infA-RP-99083-T7-TMA5-23 | 0.75 ul | 2 uM | 75 nM |
| infB-FP-99086-Flag3-23 | 0.5 ul | 2 uM | 50 nM |
| infB-RP-99089-T7-TMA5-23 | 0.5 ul | 2 uM | 50 nM |
| 447-FP-99296-Flag1-23 | 0.188 ul | 2 uM | 18.8 nM |
| 501.RP-99243-T7-2 | 0.188 ul | 2 uM | 18.8 nM |
| Total volume | 3.38 ul | | |

TABLE 7

NASBA reaction mixtures

| Component | Volume |
|---|---|
| 3X Buffer (NECB-24) | 6.7 ul |
| 6X Nucleotide (NECN-24) | 3.3 ul |
| Primer mix | 3.38 ul |
| Nuclease-Free water | 0.62 ul |
| Sample | 1 ul |
| Enzyme mix (NEC-1-24) | 5 ul |
| Total volume | 20 ul |

Step 2: Hybridization of NASBA Products to the Microarray at Room Temperature

1. Prepare the 96-well microarray plate for TMA (NASBA) hybridization. A microarray is printed at the bottom of each well. 1) Rinse each reaction well with 200 ul of molecular grade water once, followed by a 5-min 200 ul water staying in the well. 2) After aspiration of water, dispense 200 ul of pre-hybridization solution (Table 8) into the well and leave there for 5 minutes.
2. Prepare the 96-well microarray plate for TMA (NASBA) hybridization. A microarray is printed at the bottom of each well. 1) Rinse each reaction well with 200 ul of molecular grade water once, followed by a 5-min 200 ul water staying in the well. 2) After aspiration of water, dispense 200 ul of pre-hybridization solution (Table 9) into the well and leave there for 5 minutes.
3. Aspirate pre-hybridization solution, dispense 80 ul of the NASBA-hybridization solution in the well, and kept in dark for 60 minutes.
4. Wash of microarray with washing buffer (0.15×SSC). After the hybridization, aspirate the hybridization solution and wash wells four times. One time rinse followed by a 10-min wash (keep washing buffer in the well for 10-min), then 2× rinse. Dry the plate by spinning the plate face down in a Micro Array Plate Centrifuge for 3-5 minutes.

TABLE 8

Pre-hybridization Buffer

| 96-Well Plate | Volumes needed for 8 wells to be pre-hybridized |
|---|---|
| Molecular biology grade water | 1.397 mL |
| Pathogen Dx DetectX Buffer 1 (20X SSC) | 0.415 mL |
| PathogenDx DetectX Buffer 2 (50X Denhardt's) | 0.218 mL |

TABLE 9

PDx NASBA microarray hybridization mixture

| | Volume | Stock concentration |
|---|---|---|
| Product of NASBA reaction | 20 ul | |
| 20X SSC | 7 ul | |
| 50X Denhardt's solution | 7 ul | |
| Biotin-Flag1 | 0.64 ul | 50 uM |
| Biotin-Flag3 | 1.28 ul | 50 uM |
| Biotin-TMA5 | 0.64 ul | 50 uM |
| Biotin-Amp6 | 0.64 ul | 50 uM |
| SAPE | 42.8 ul | 2.5 uM |
| Total volume | 80 ul | |

Step 3: Scanning the Microarray and Data Acquisition.
1. Scan the hybridized microarray plate in a desktop Sensovation scanner using the "PathogenDx™ Assay 002" program.
2. Submit the "Scan Results" file folder to the "Image Folder" in the PDx Dropbox.
3. The folder automatically begins to upload, and the Augury™ Software analyzes the data and directly deposits the reports into the "Reports" folder within Dropbox.
4. The relative fluorescent units (RFU) of hybridized signals corresponding to different probes on the microarray can be obtained with the "Rearrange-DotScore" software analyzing the PAX file in the "Reports" folder.

Figure 8:
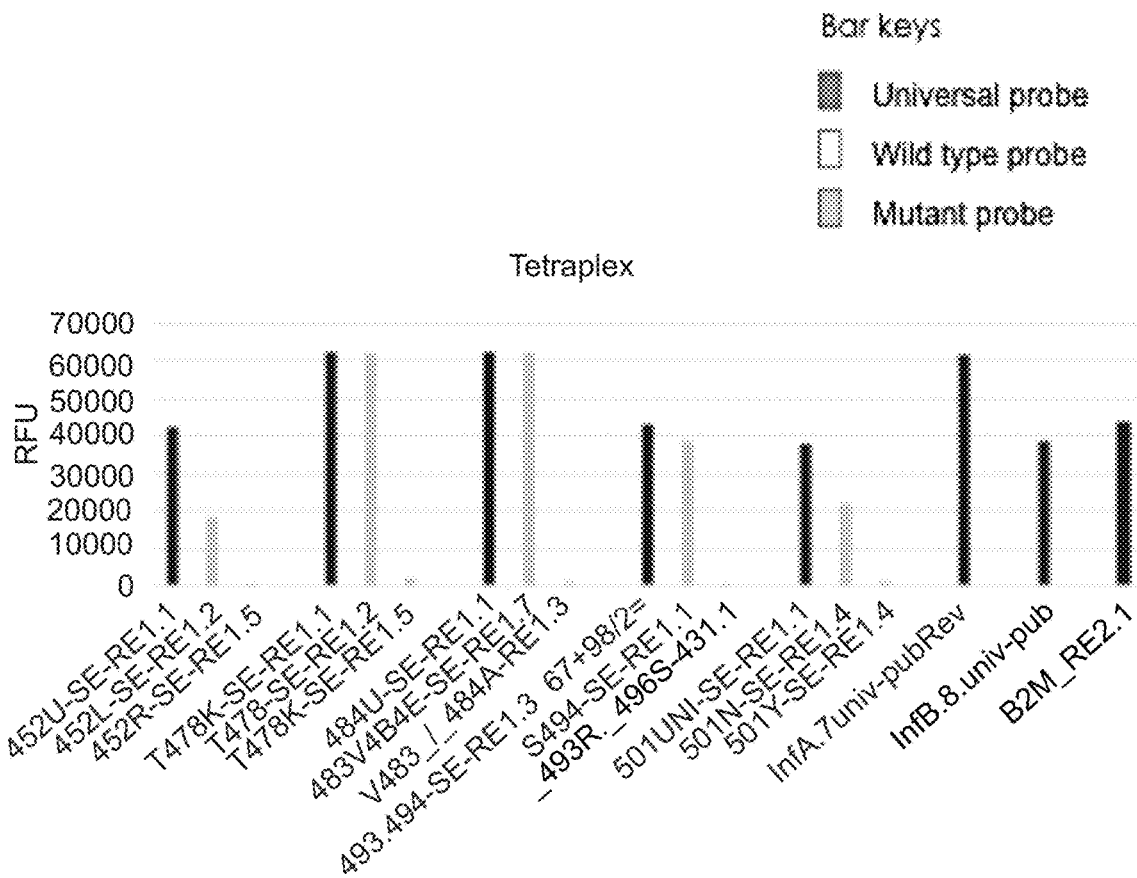
FIG. 8 shows the relative fluorescent unit (RFU) of hybridization signals derived via the method provided herein of SARS-Cov-2 (with multiple probes), influenza A, influenza B, and B2M. Templates are genomic RNA of each virus and Human Reference RNA for B2M. 10,000 genome copies/reaction of templates are used. SARS-Cov-2 genomic RNA is from wild type (Wuhan strain) of CoV-2, influenza A gRNA is from H1N1 influenza A subtype, and influenza B gRNA is from Yamagata lineage of influenza B.
Figure 9A:
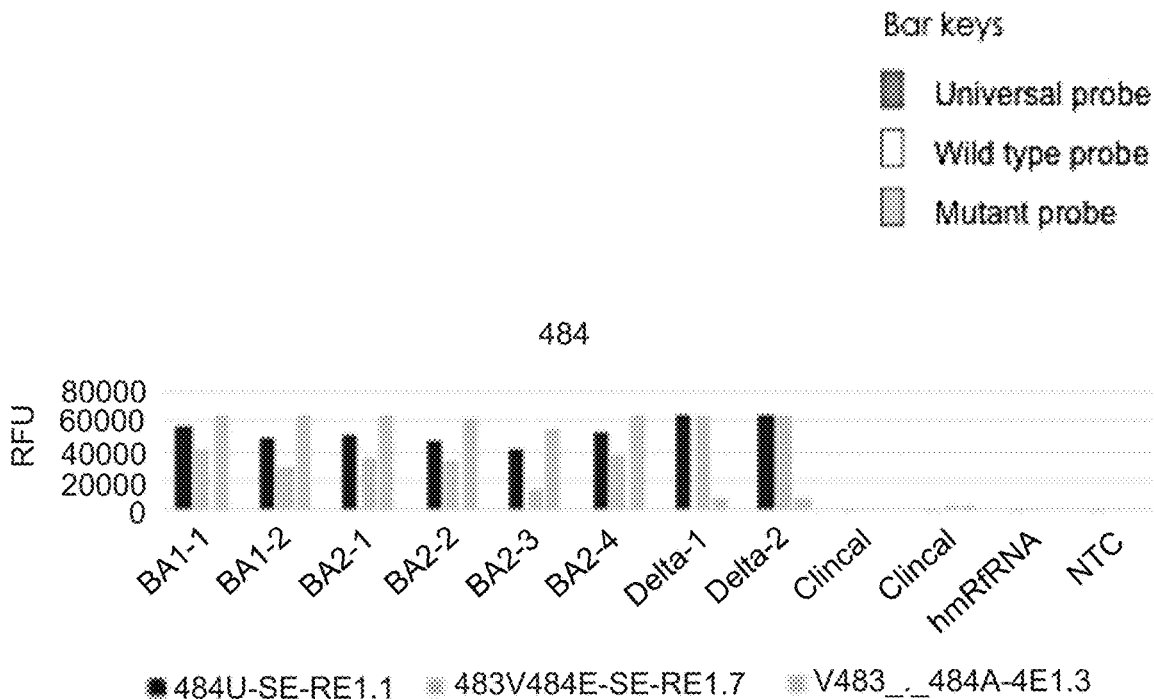
FIGS. 9A-9E show the relative fluorescent unit (RFU) of hybridization signals derived via the method provided herein from SARS-Cov-2 clinical positive and negative samples, including 2 Omicron BA1 (BA1-1, BA1-2), 4 Omicron BA2 (BA2-1, BA2-2, BA2-3, BA2-4), 2 Delta (Delta-1, Delta-2), 2 clinical negative (Clinical Neg-1, Clinical Neg-2), 1 Human-reference-RNA (hmRfRNA), and a No-Template-Control (NTC).
Figure 9B:
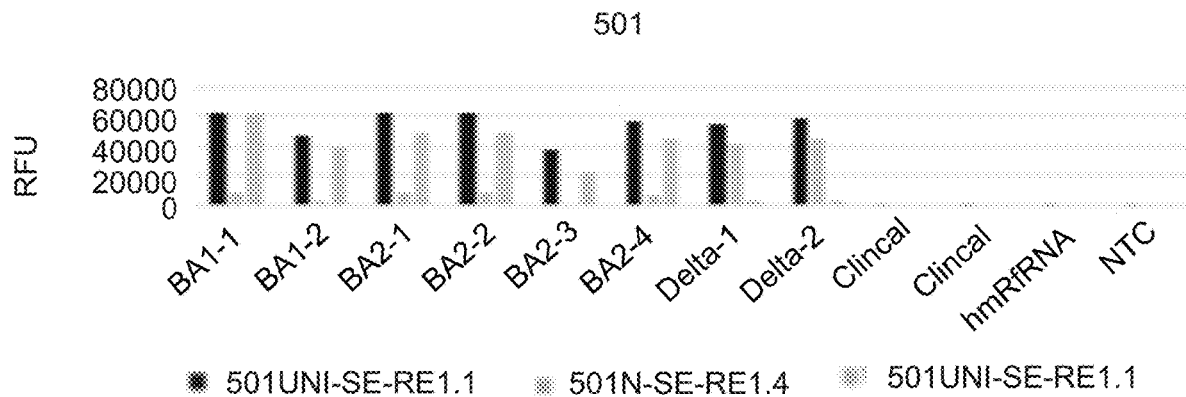
Figure 9C:
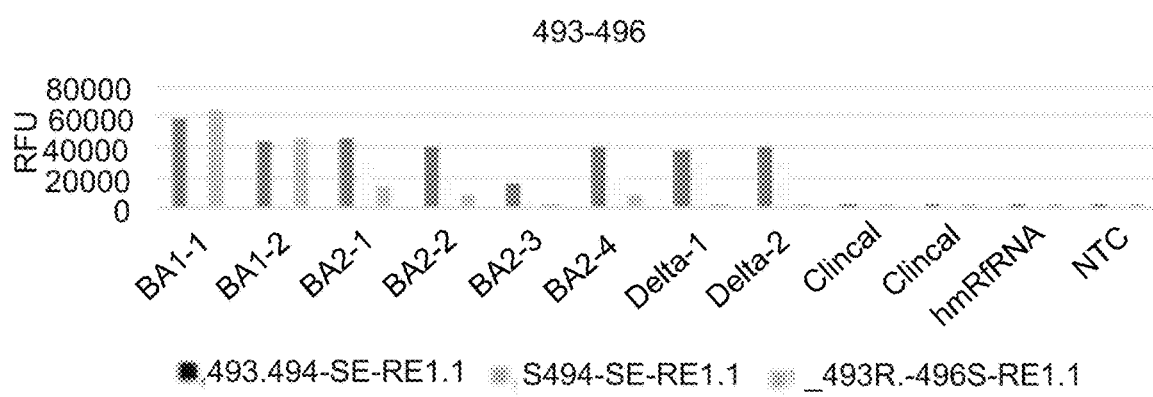
Figure 9D:
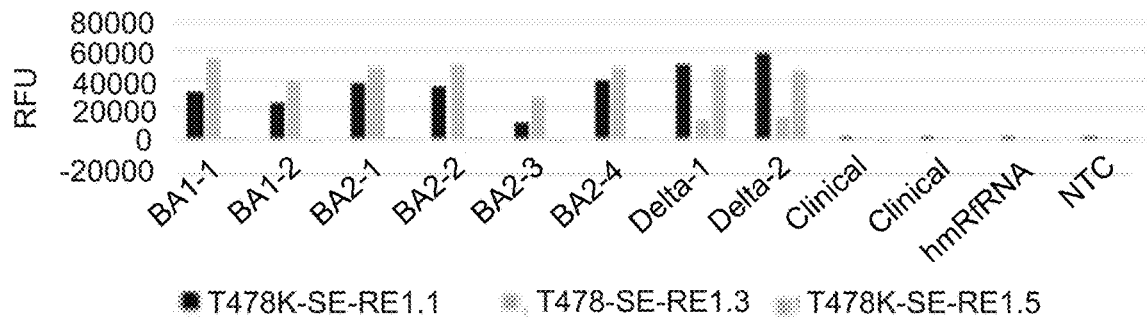
Figure 9E:
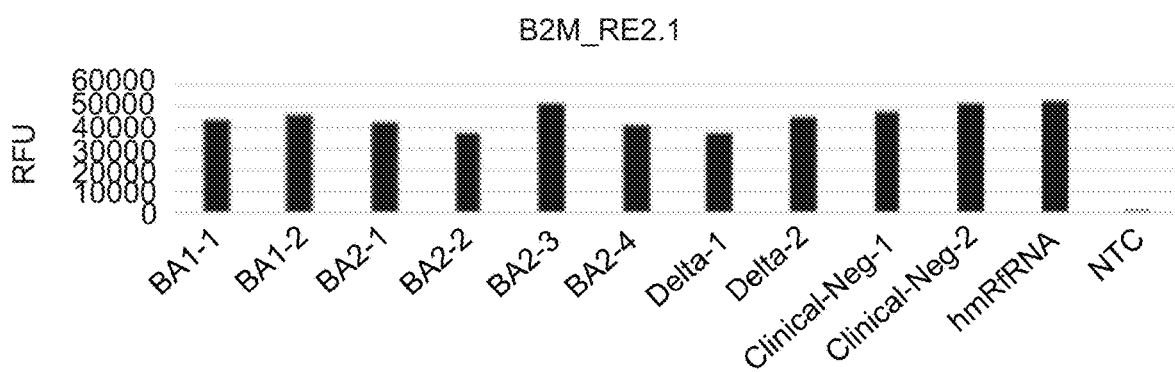
Figure 10A:
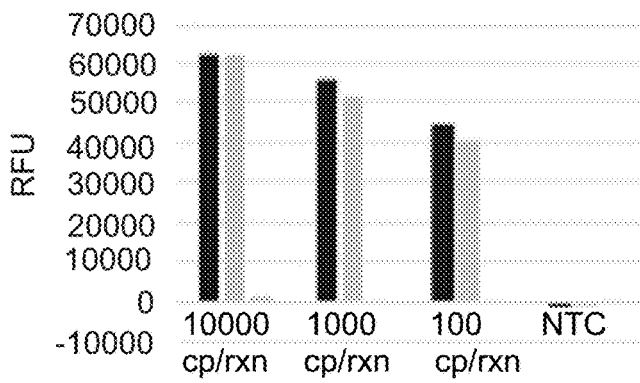
FIGS. 10A-10C show the relative fluorescent unit (RFU) of hybridization signals derived via the method provided herein from SARS-Cov-2 genomic RNA at concentration of 10,000, 1000, and 100 genome copies/reaction.
Figure 10B:
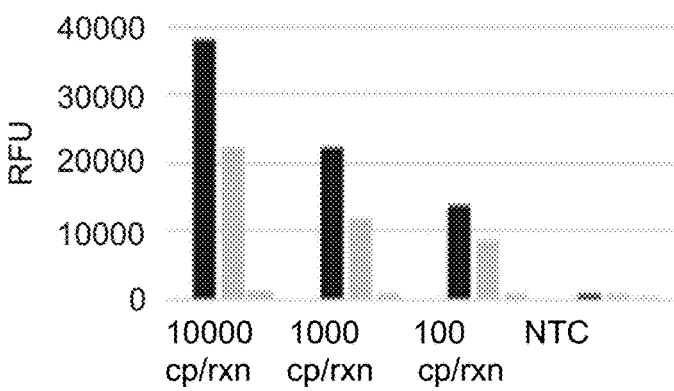
Figure 10C:
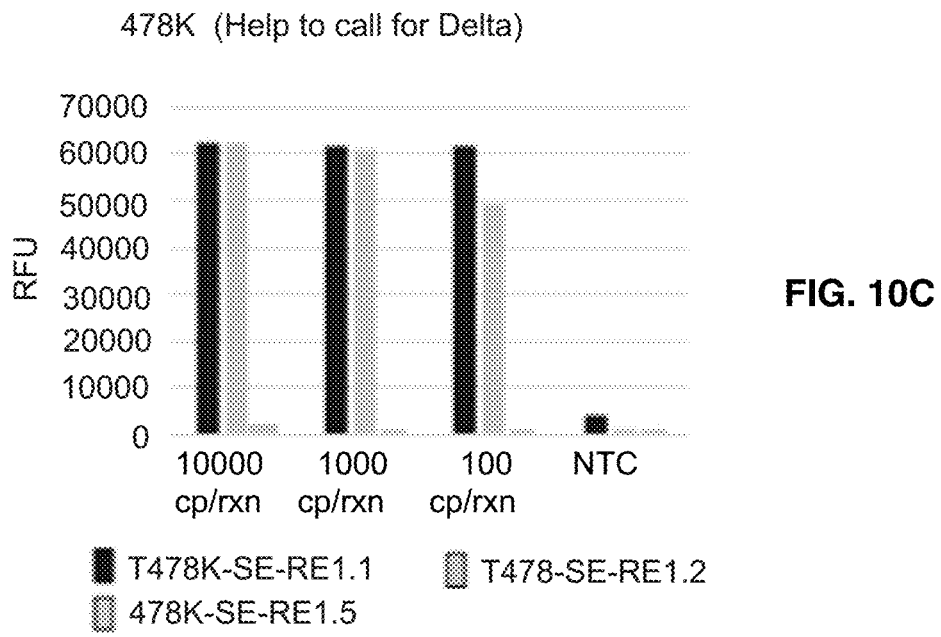
Figure 11:
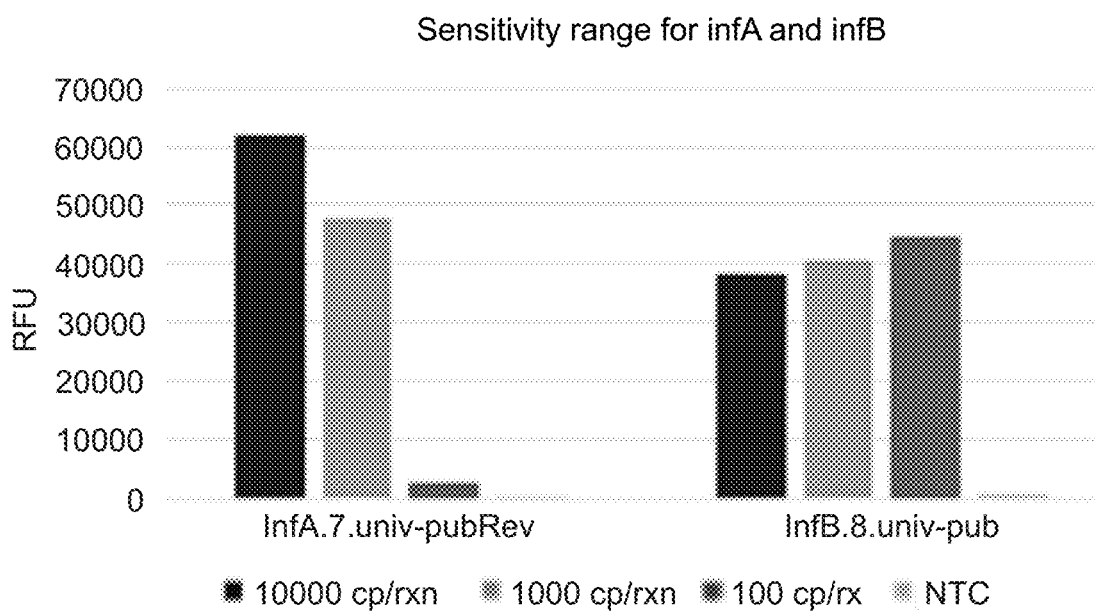
FIG. 11 shows the relative fluorescent unit (RFU) of hybridization signals derived via the method provided herein from SARS-Cov-2 genomic RNA at concentration of 10,000, 1000, and 100 genome copies/reaction.
Figure 12A:
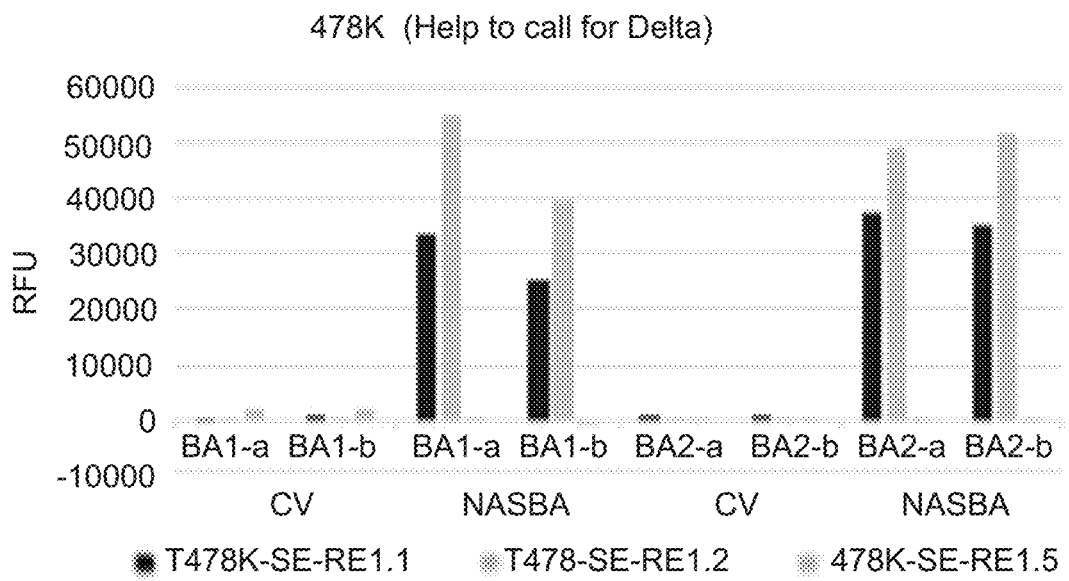
FIGS. 12A-12B show the relative fluorescent unit (RFU) of hybridization signals derived via the method provided herein from 2 of SARS-Cov-2 Omicron BA-1 and 2 BA-2 clinical samples detected by PDx-NASBA and PDx-Detect-CV+ assays.
Figure 12B:
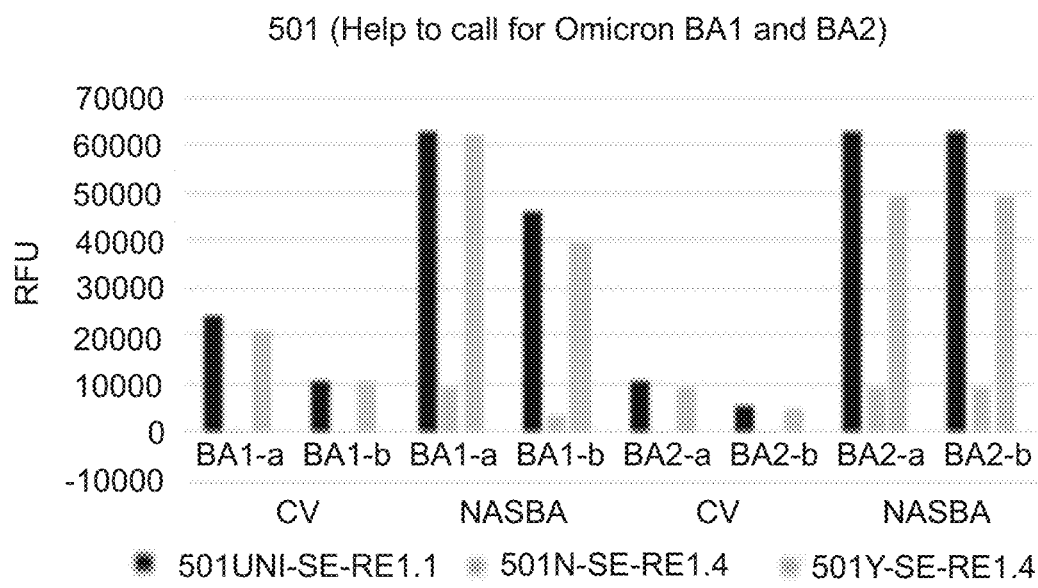

The multiplex TMA (NASBA) technology, coupled to microarray detection detects and resolves a mixture of viral genomes, i.e., SARS-CoV-2, influenza A, and influenza B RNA, and also purified human RNA (B2M gene) as a single multiplex reaction (FIG. 8). The multiplex NASBA-Microarray technology also distinguishes SARS-CoV-2 Variants including Omicron BA1, BA2, and Delta (FIGS. 9A-9E) based on the unique pattern of single nucleotide polymorphism presented within the region of the Spike gene that has been amplified in the present multiplex NASBA reaction. This observation confirms that the present method is suitable to yield RNA amplicons which may be successfully analyzed by microarray hybridization, under hybridization conditions where sequences can be resolved based on a single nucleotide change. When coupled to microarray analysis, these data reveal an analytical LOD for the multiplex NASBA reaction of 100 genome copies/reaction for SARS-CoV-2 and influenza B, and 1000 genome copies/reaction influenza A (FIGS. 10A-10C and FIG. 11). Direct comparison of the present multiplex NASBA reaction with a multiplex RT-PCR reaction which has been designed to amplify the same Spike gene region (FIGS. 12A-12B) shows that the multiplex NASBA reaction of the present invention can be as sensitive as a multiplex RTPCR predicate in detecting SARS-CoV-2 Omicron variant BA1 in clinical samples.

Figure 13A:
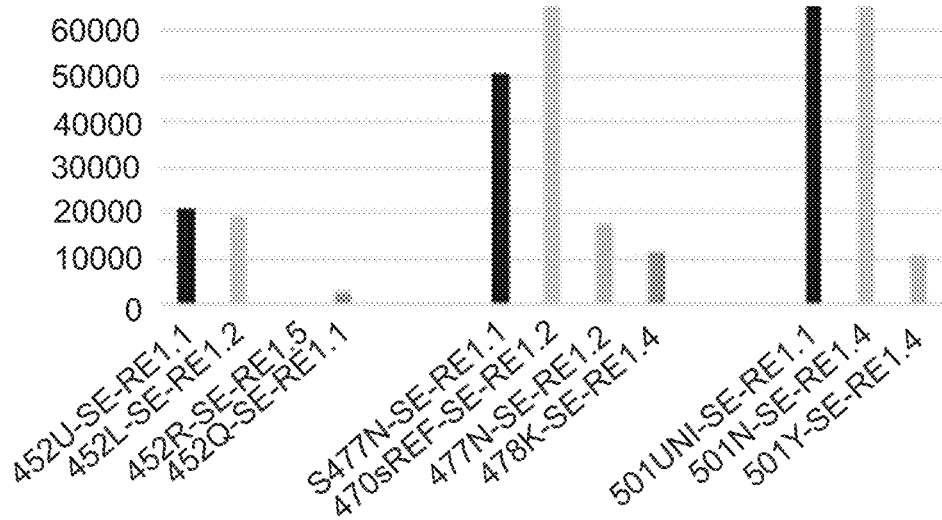
FIGS. 13A-13B show the relative fluorescent unit (RFU) of hybridization signals derived via the method provided herein from detection of SARS-Cov-2 wild type (Wuhan) genomic RNA at 40,000 genome copies/reaction with single plex primer set. In the SAPE detection, biotinylated detector probe binds with SAPE (Streptavidin, R-Phycoerythrin conjugate) (FIG. 13A) to show fluorescent signals, while in the Cy3 detection (FIG. 13B), Cy3 labeled detector probe shows fluorescent signals.
Figure 13B:
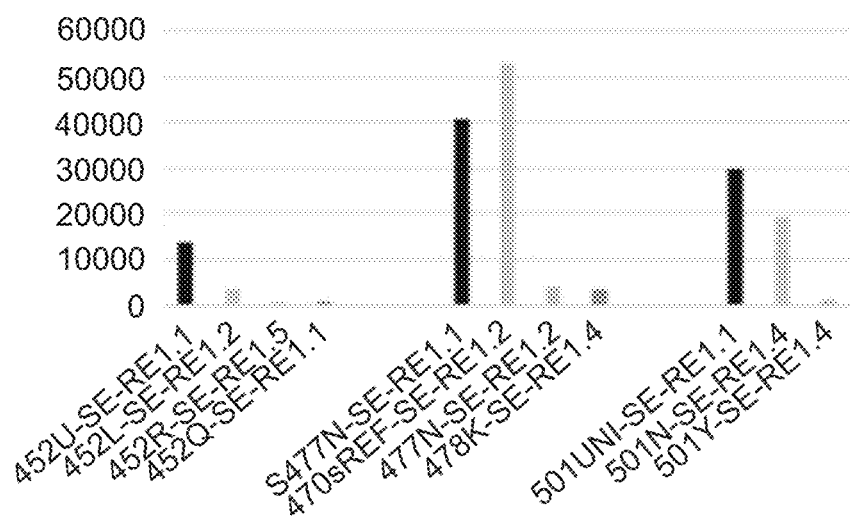

Also shown is that a biotinylated detector probe may be used which, upon binding to SAPE (Streptavidin, R-Phycoerythrin conjugate) multiplex NASBA amplicon binding to microarray probes, may be detected via the resulting fluorescent SAPE fluorescence signals, with sensitivity similar to that obtained with identical detector probes labeled covalently at time of their synthesis with CY3 dye. The data (FIGS. 13A-13B) shows that such non-covalent SAPE labeling is more sensitive than direct covalent labeling of the detector probe with an organic fluor such as CY3. The data also suggest that other types of detection methods, such as other organic fluors or phosphors or ceramic Quantum Dots, may be similarly used to detect hybridization of multiplex NASBA amplicons via the creation of a streptavidin conjugate and its (analogous) binding to biotin modification on the detector probe.

Example 4

Multiplex NASBA Microarray Detection of Ribosomal RNA Hypervariable Regions in Prokaryotes or Eukaryotes It is well known in the art that in bacteria and more generally prokaryotes and in fungi and more generally eukaryotes that the ribosomal RNA (rRNA) 16s and 23S in prokaryotes and 18S and 28S in eukaryotes each contain hypervariable regions which during the course of evolution have developed patterns of sequence variation within them which can be used to distinguish prokaryotic and eukaryotic genera and, in many cases, to resolve species within those prokaryotic and eukaryotic genera. It is also well known in the art that those hypervariable regions are flanked in most cases by highly conserved sequences, i.e., sequences which do not vary greatly among bacteria and eukaryotes. As a result, it is also well known that universal PCR primers and universal" isothermal amplification primers can be designed so that a single universal primer pair may be used to amplify, by PCR or by isothermal amplification, each of the known hypervariable regions in prokaryotes and in eukaryotes so that the sequence of the resulting amplicons may then be analyzed to determine the identity of the cells or tissues or organisms in the sample under analysis. It is demonstrated that a well-known bacterial hypervariable region (HV3) for which universal PCR primer pairs are well known is similarly amplified by use of a corresponding multiplex TMA (NASBA) primer pair, designed as provided herein, thus enabling multiplex TMA (NASBA) amplification of one or more such hypervariable ribosomal RNA sites as a single multiplex isothermal amplification reaction.

Table 10 identifies an optimized PCR primer pair sequence (16SFP, 16SRP) and the corresponding multiplex NASBA primer pair sequence (16SFP-Flag3, 16SRP-T7+TMA5-23). The main distinction between the PCR vs the corresponding multiplex NASBA primer pair is the introduction of a flanking sequence in one NASBA primer which upon reverse transcription and the action of RNAse H generates a T7 promoter and a first detector probe binding site (16SRP-T7+TMA5-23) at one end of the resulting RT+RNase H double stranded DNA product. In turn, the other member of the NASBA primer pair creates a single detector probe binding site at the opposite end of the resulting double stranded DNA RT+RNase H product (16SFP-Flag3).

TABLE 10

Representative multiplex TMA (NASBA) primers, detector probes and hybridization probe for rRNA Analysis

| SEQ ID NO | Sequence Name | Sequences |
|---|---|---|
| | PCR primer | |
| 113 | 16SFP | CACACTGGRACTGAGACACG |
| 114 | 16SRP | GTATTACCGCGGCTGCTGGCA |
| | NASBA primer | |
| 115 | 16SFP-Flag3 | TTTCTACCGTACTCTAGCTA-CACACTGGRACTGAGACACG |
| 116 | 16SRP-T7+ TMA5-23 | GAATTTAATACGACTCACTATAGGGATAACTCAACAG-GTATTACCGCGGCTGCTGGCA |
| | Detector Probe | |
| 108 | Flag3-Biot 100 | /5Biosg/TTTCTACCGTACTCTAGCTTT |
| 109 | TMA5-15MER-BIOT | /5Biosg/TTTCTGTTGAGTTATCCCTTT |
| | *Listeria* spp. hybridization probe for PCR & NASBA amplicons | |

As described herein, upon the action of T7 polymerase, multiple RNA amplicons are produced from such a multiplex TMA (NASBA) primer pair, resulting from the combined action of [RT+RNaseH+T7]. Moreover, those RNA amplicon molecules are then ready to hybridize to a cognate nucleic acid probe, which, upon ordinary Watson-Crick pairing, can be used to identify the genera or the species associated with the rRNA template of interest in the original sample. One such representative hybridization probe is described (*Listeria* spp. hybridization probe) which upon hybridization to such a multiplex NASBA amplicon specifically identifies the sample as containing rRNA from one of the several known *Listeria* species, that is, the probe identifies the sample as "*Listeria* spp".

As described herein, several TMA (NASBA) primer pairs like those in Table 10 may be deployed in parallel to amplify a larger set of rRNA hypervariable sites as a single multiplex TMA (NASBA) reaction. The amplified RNA product of each element of such a multiplex TMA (NASBA) reaction in turn is then hybridized in parallel to a single microarray containing many hybridization probes, like those in Table 10. In that way, a combination of multiplex TMA (NASBA) amplification at multiple hypervariable sites in bacteria and in eukaryotes produce multiple RNA amplicons in parallel which then bind by sequence specific hybridization to a very large number of hybridization probes arrayed on a surface of a microarray. The resulting pattern of microarray hybridization, as visualized by the binding of fluorescently tagged detector probes to the detector probe binding sites created at the end of the RNA amplicons may then be used to identify which bacteria and fungi are present in a sample, based on the measured pattern of binding to the microarray. Samples of interest suitable for analysis are a surface swab, an air sample, a food sample, a blood sample or a urine sample or any other biological or environmental sample for which an understanding of its microbial content would be valuable.

REFERENCES

1. Scheler et al. BMC Biotechnol, 9:45. (2009 May 15).
2. Scheler et al. BMC Biotechnol. 11:17 (2011).
3. van Gemen et al. J Virol Methods, 49(2):157-167 (1994).
4. Gill et al. Biochemical and Biophysical Research Communications, 347(4):1151-1157 (2006).
5. Ghalami M and Tehrani HA. Biochemical and Biophysical Research Communications, 347(4):1151-1157 (2006).
6. Morisset et al. Nucl Acids Res, 36(18):e118 (2008).
7. Yan et al. Mol Biosyst. 10(5):970-1003 (2014 May).
8. Asiello, P J and Baeumner, A J. Lab Chip, 11(8):1420-30 (2011 Apr. 21).
9. Morisset et al. Nucleic acids research, 36:e118 (2008).
10. Mader et al. Analytical and bioanalytical chemistry, 397:3533-3541 (2010).
11. Scheler et al. BMC biotechnology, 9:45 (2009).
12. Kaplinski et al. BMC biotechnology, 10:34 (2010).
13. Jauset-Rubio et al. Sci Rep 6, 37732 (2016).

What is claimed is:

1. A method for detecting a COVID-19 virus in a sample comprising:
   a) obtaining the sample;
   b) isolating crude nucleic acids therefrom;
   step (c), performing, on the crude nucleic acids, a combined isothermal reverse transcription, RNAse H and isothermal RNA amplification reaction using at least one forward primers and at least one reverse primers wherein the reverse primer comprises a detector probe sequence with a nucleotide sequence selected from the group consisting of SEQ ID NO: 98, SEQ ID NO:99, SEQ ID NO: 100 and SEQ ID NO: 101 that binds to a fluorescent labeled detector probe nucleotide sequence to generate a plurality of single stranded RNA amplicons each comprising a sequence complementary to the fluorescent labeled detector probe nucleotide sequence at the 5' end, the 3' end or a combination thereof of each of the plurality of RNA amplicons; and
   d) hybridizing, at an ambient temperature, the plurality of single-stranded RNA amplicons to a plurality of the fluorescent labeled detector probes and a plurality of hybridization probes each comprising a nucleotide sequence complementary to a sequence determinant in the COVID-19 virus, said hybridization probes attached to a solid microarray support;
   e) washing the microarray support at least once; and
   f) imaging the microarray support to detect at least one fluorescent signal from at least one of the plurality of fluorescent labeled detector probes, thereby detecting the COVID-19 virus in the sample.

2. The method of claim 1, further comprising isolating total RNA or mRNA after step b, and step c comprising performing the combined isothermal reverse transcription, RNAse H and isothermal RNA amplification reaction on the total RNA.

3. The method of claim 1, further comprising calculating an intensity of the fluorescent signal, said intensity correlating with a copy number of the COVID-19 virus in the sample.

4. The method of claim 1, wherein the at least one forward primer comprises the nucleotide sequences selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, and SEQ ID NO: 15 and the at least one forward primer comprises the nucleotide sequences selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, and SEQ ID NO: 16.

5. The method of claim 1, wherein the plurality of hybridization probes comprises the nucleotide sequences selected from the group consisting of SEQ ID NOS: 17-22, SEQ ID NOS: 23-27, SEQ ID NOS: 28-33, SEQ ID NOS: 34-40, SEQ ID NOS: 41-47, SEQ ID NOS: 48-56, SEQ ID NOS: 57-67, SEQ ID NOS: 74-77, SEQ ID NOS: 78-81, SEQ ID NOS: 82-86, SEQ ID NOS: 87-89, SEQ ID NOS: 90-94, SEQ ID NOS: 95-97 and a combination thereof.

6. The method of claim 1, wherein the fluorescent labeled detector probe is in a molar ratio of 0.1 to 5 with the single-stranded RNA amplicons.

7. The method of claim 1, wherein the ambient temperature is about 15° C. to about 30° C.

8. The method of claim 1, wherein the COVID-19 virus is a wild type COVID-19 virus or a clade variant thereof.

9. The method of claim 8, wherein the clade variant is B.1.2, B.1.1.7, B.1.351, B.1.375, B.1.427, B.1.429, B.1.525, B.1.526P1, P2, Wuhan, or a combination thereof.

10. The method of claim 1, wherein the sample comprises at least one of a nasopharyngeal swab, a nasal swab, a mouth swab, a mouth wash, a blood sample, a biopsy sample, an aerosol, or a hard surface swab.

11. A method for detecting an RNA of interest in a sample comprising:
a) obtaining the sample;
b) isolating nucleic acids from the sample;
c) performing on the nucleic acids, a combined isothermal reverse transcription and isothermal RNA amplification reaction using at least one forward primer and at least one reverse primer wherein the reverse primer comprises a detector probe with a nucleotide sequence that binds to the fluorescent labeled detector probe to generate single stranded RNA amplicons each comprising a sequence complementary to the fluorescent labeled detector probe nucleotide sequence; wherein the detector probe nucleotide sequence is selected from the group consisting of SEQ ID NO 98, 99, 100, 101, 108 and 109 and a combination thereof;
d) hybridizing the single-stranded RNA amplicons to at least one of the fluorescent labeled detector probes and at least one hybridization probe comprising a nucleotide sequence complementary to a sequence determinant in the RNA of interest, said at least one hybridization probe attached to a solid microarray;
e) washing the microarray at least once; and
f) imaging the microarray to detect at least one fluorescent signal from at least one of the plurality of fluorescent labeled detector probes, thereby detecting the RNA of interest in the sample.

12. The method of claim 11, further comprising calculating an intensity of the fluorescent signal, said intensity correlating with a copy number of the RNA of interest in the sample.

13. The method of claim 11, wherein the nucleic acids are crude nucleic acids, total RNA, mRNA, or ribosomalRNA.

14. The method of claim 11, wherein the fluorescent labeled detector probe is in a molar ratio of 0.1 to 5 with the single-stranded RNA amplicons.

15. The method of claim 11, wherein the RNA of interest is a pathogenic viral RNA and is isolated from a Severe Acute Respiratory Syndrome Coronavirus 2 (COVID-19 virus), a Respiratory Syncytial Virus, a Middle East Respiratory Syndrome coronavirus (MERS-COV), a Severe Acute Respiratory Syndrome Coronavirus (SARS-COV), a 229E Coronavirus, a OC43 Coronavirus, a NL63 Coronavirus, a HKU1 Coronavirus, an Influenza A virus, or an Influenza B virus or a combination thereof.

16. The method of claim 15, wherein the pathogenic viral RNA is isolated from a wild type COVID-19 virus or a clade variant that is B.1.2, B.1.1.7, B.1.351, B.1.375, B.1.427, B.1.429, B.1.525, B.1.526, P1, P2, or Wuhan, or a combination thereof.

17. The method of claim 11, wherein the at least one forward primer is selected from the group consisting of the nucleotide sequences of SEQ ID NO: 1, SEQ ID NO: 3, SEQ ID NO: 5, SEQ ID NO: 7, SEQ ID NO:9, SEQ ID NO: 11, SEQ ID NO: 13, SEQ ID NO: 15, SEQ ID NO: 102, 105, SEQ ID NO: 110, and a combination thereof and the at least one reverse primer is selected from the group consisting of the nucleotide sequences of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16 SEQ ID NO: 103 106, SEQ ID NO:111, and a combination thereof.

18. The method of claim 11, wherein the at least one hybridization probe is selected from the group consisting of the nucleotide sequences of SEQ ID NOS: 17-22, SEQ ID NOS: 23-27, SEQ ID NOS: 28-33, SEQ ID NOS: 34-40, SEQ ID NOS: 41-47, SEQ ID NOS: 48-56, SEQ ID NOS: 57-67, SEQ ID NOS: 74-77, SEQ ID NOS: 78-81, SEQ ID NOS: 82-86, SEQ ID NOS: 87-89, SEQ ID NOS: 90-94, and SEQ ID NOS: 95-97, SEQ ID NO: 104, SEQ ID NO: 107, SEQ ID NO: 112, and a combination thereof.

19. The method of claim 12, wherein the RNA of interest is a pathogenic viral RNA and is isolated from an Influenza A virus.

20. The method of claim 19, wherein the at least one forward primer comprises the nucleotide sequence of SEQ ID NO: 102 and the reverse primer comprises the nucleotide sequence of SEQ ID NO: 103.

21. The method of claim 19, wherein the at least one hybridization probe comprises the nucleotide sequences of SEQ ID NO: 104.

22. The method of claim 11, wherein the RNA of interest is a pathogenic viral RNA and is isolated from an Influenza B virus.

23. The method of claim 22, wherein the forward primer comprises the nucleotide sequence of SEQ ID NO: 105 and the reverse primer comprises the nucleotide sequence of SEQ ID NO: 106.

24. The method of claim 22, wherein the at least one hybridization probe comprises the nucleotide sequence of SEQ ID NO: 107.

25. The method of claim 11, wherein the sample comprises at least one of a nasopharyngeal swab, a nasal swab, a mouth swab, a skin swab and vaginal swab, a mouth wash, a skin wash, a plant wash, a homogenized food sample, a blood sample, a biopsy sample, an aerosol, or a hard surface swab.

* * * * *